United States Patent
Sherr et al.

(10) Patent No.: US 10,314,810 B2
(45) Date of Patent: *Jun. 11, 2019

(54) ARYL HYDROCARBON RECEPTOR (AHR) MODIFIERS AS NOVEL CANCER THERAPEUTICS

(75) Inventors: David H. Sherr, West Roxbury, MA (US); Michael Pollastri, Waltham, MA (US); Jennifer Schlezinger, East Falmouth, MA (US); Sarah Haigh Molina, Boston, MA (US); Scott Schaus, Boston, MA (US); Joshua Robert Giguere, Sharon, MA (US)

(73) Assignees: Trustees of Boston University, Boston, MA (US); Northeastern University, Boston, MA (US); Boston Medical Center Corporation, Boston, MA (US)

( * ) Notice: Subject to any disclaimer, the term of this patent is extended or adjusted under 35 U.S.C. 154(b) by 644 days.

This patent is subject to a terminal disclaimer.

(21) Appl. No.: 13/812,375

(22) PCT Filed: Jul. 27, 2011

(86) PCT No.: PCT/US2011/045526
§ 371 (c)(1),
(2), (4) Date: Jul. 11, 2013

(87) PCT Pub. No.: WO2012/015914
PCT Pub. Date: Feb. 2, 2012

(65) Prior Publication Data
US 2013/0281525 A1 Oct. 24, 2013

Related U.S. Application Data

(60) Provisional application No. 61/368,042, filed on Jul. 27, 2010.

(51) Int. Cl.
| | |
|---|---|
| A61K 31/352 | (2006.01) |
| C07D 311/22 | (2006.01) |
| C07D 407/04 | (2006.01) |
| A61K 31/35 | (2006.01) |
| A61K 45/06 | (2006.01) |

(52) U.S. Cl.
CPC ............ *A61K 31/352* (2013.01); *A61K 31/35* (2013.01); *A61K 45/06* (2013.01); *C07D 311/22* (2013.01); *C07D 407/04* (2013.01)

(58) Field of Classification Search
None
See application file for complete search history.

(56) References Cited

U.S. PATENT DOCUMENTS

| | | | |
|---|---|---|---|
| 4,065,574 A | 12/1977 | Moon et al. | |
| 4,127,669 A * | 11/1978 | Connor | C07D 311/22 514/456 |
| 4,143,145 A * | 3/1979 | Doria | C07D 311/22 514/337 |
| 4,152,449 A * | 5/1979 | Doria | C07D 311/22 514/456 |
| 4,177,276 A * | 12/1979 | Doria | C07D 311/22 514/337 |
| 4,177,286 A * | 12/1979 | Doria | C07D 311/22 514/456 |
| 4,183,945 A * | 1/1980 | Doria | C07D 311/22 514/456 |
| 4,183,946 A * | 1/1980 | Doria | C07D 311/22 514/456 |
| 5,919,820 A * | 7/1999 | Moesgaard | A61K 31/375 514/474 |
| 6,066,642 A | 5/2000 | Jacobson et al. | |
| 6,180,661 B1 | 1/2001 | Eugster et al. | |
| 6,346,626 B1 | 2/2002 | Billich et al. | |
| 6,468,991 B1 * | 10/2002 | Budowsky | A61K 31/7048 514/81 |
| 7,098,376 B2 | 8/2006 | Poellinger et al. | |
| 7,419,992 B2 | 9/2008 | Deluca et al. | |
| 7,569,352 B2 | 8/2009 | Von Stein et al. | |
| 2006/0142211 A1 | 6/2006 | Mao-Hsiung et al. | |
| 2009/0130051 A1 * | 5/2009 | Jarrott | A61K 31/352 424/78.32 |

FOREIGN PATENT DOCUMENTS

| | | |
|---|---|---|
| JP | 2004123728 A | 4/2004 |
| WO | 98/11889 | 3/1998 |
| WO | 01/21608 A2 | 3/2001 |
| WO | 2001021608 A2 | 3/2001 |
| WO | 2009/115807 A1 | 9/2009 |

(Continued)

OTHER PUBLICATIONS

STN Registry No. 819827-50-4. "2-{[2-(5-bromo-2-furyl)-4-oxo-4H-chromen-3-yl]oxy}acetamide". STN Database. Jan. 25, 2005. One Page.*
Patani et al. "Bioisosterism: A Rational Approach in Drug Design". Chem Rev. Dec. 1996 96(8):3147-3176.*
Silverman RB. "The Organic Chemistry of Drug Design and Drug Action". Section 2.2. 2004. pp. 29-32.*
Conti et al. "Anti-Picornavirus Activity of Synthetic Flavon-3-yl Esters". Antiviral Chemistry & Chemotherapy. 1998; 9(6):511-515. ( Year: 1998).*

(Continued)

*Primary Examiner* — Leslie A. Royds Draper
(74) *Attorney, Agent, or Firm* — Nixon Peabody LLP

(57) ABSTRACT

Provided herein are novel agents that modulate AhR activity for use in therapeutic compositions and methods thereof for inhibiting cancer cell proliferation and tumor cell invasion and metastasis. The agents comprise AhR inhibitors or non-constitutive AhR agonists of Formula (I) and (II) for the inhibition of cancer cell growth and parameters that characterize tumor metastasis, such as tumor cell invasiveness.

4 Claims, 13 Drawing Sheets
Specification includes a Sequence Listing.

(56) References Cited

FOREIGN PATENT DOCUMENTS

| WO | 2009115807 A1 | 9/2009 |
|----|---------------|--------|
| WO | 2010/008731 A1 | 1/2010 |
| WO | 2010/058242 A1 | 5/2010 |
| WO | 2010058242 A1 | 5/2010 |

OTHER PUBLICATIONS

Otava Chemicals. [Online]. "Screening Compounds for Prompt Delivery". [Retrieved Jan. 19, 2017]. Retrieved from the Internet: < URL: http://www.otavachemicals.com/products/compound-libraries-for-hts/screening-collection-for-prompt-delivery>. Two pages.*
Google Indexing for Otava Chemicals. "Screening Compounds for Prompt Delivery". Availability Date of Apr. 6, 2008.*
Balakin et al. "In Silico Estimation of DMSO Solubility of Organic Compounds for Bioscreening". Journal of Biomolecular Screening. 2004; 22-31. (Year: 2004).*
Thakar et al. "Synthesis of Fural Analogs of Substituted Flavonoids". J. Indian Chem. Soc. 1973; vol. L, p. 420-423. (Year: 1973).*
Ashida, et al., "Flavones and Favonols at dietary levels inhibit a transformation of arylhydrocarbon receptor induced by dioxin", FEBS Letters, 476(3)213-217 (2000).
Danfeng et al., "Aryl hydrocarbon receptor and breast cancer", J. Med. Mol. Biol, 4(6):531-533 (2007).
Database CAPLUS—Jayashree et al., Synthesis of substituted 3-hydroxy flavones for antioxidant and antimicrobial activity, XP002721712, retrieved from STN Database accession No. 2009:58730.
Funayama et al., "Cytocidal and Antimicrobial Activities of Flavonoid", Natural Medicines, 149(3) p. 322-328 (1995).
Park et al., "Suppressive effects of ethanolic extracts from propolis and its main botanical origin on dioxin toxicity." Journal of Agricultural and Food Chemistry, 53(26):10306-10309 (2005).
Pica et al., "Pentasubstituted quercetin analogs as selective inhibitors of particulate 3',5'-cyclic-AMP phosphodiesterase from rat brain." Journal of Medicinal Chemistry, 25(10):1192-1198 (1982).
Pliskova et al., "Effects of silymarin flavonolignans and synthetic silybin derivatives on estrogen and aryl hydrocarbon receptor activation." Toxicology, (1-2):80-89 (2005).
Reiners et al., "PD98059 is an Equipotent Antagonist of the Aryl Hydrocarbon Receptor and Inhibitor of Mitogen-Activated Protein Kinase Kinase", Molecular Pharmcology 53:438-445 (1998).
Swanson et al., "Use of [125I]4'-iodoflavone as a tool to characterize ligand-dependent differences in Ah receptor behavior." Journal of Biochemical and Molecular Toxicology, 16(6):298-310 (2002).
Henry, E.C., et al., Flavone antagonists bind competitively with 2, 3, 7, 8-tetrachlorodibenzo-p-dioxin (TCDD) to the aryl hydrocarbon recepto but inhibit nuclear uptake and transformation, Molecular Pharmacology, American Society for Pharmacology and Experimental Therapeutics, US, vol. 55, No. 4, Apr. 1, 1999, pp. 716-725, XP002447278, ISSN: 0026-895X.
Swanson, H., et al., Use of [125I]4-iodoflavone as a tool to characterize ligand-dependent differences in Ah receptor behavior, Journal of Biochemical and Molecular Toxicology, Wiley, New York, NY, US, vol. 16, No. 6, Jan. 1, 2002, pp. 298-231, XP002536477, ISSN: 1099-0461, DOI: 10.1002/JBT.10053.
Yong, K., et al., Suppressive effects of ethanolic extracts from propolis and its main botanical origin on Dioxin Toxicity, Journal of Agricultural and Food Chemistry, vol. 53, No. 26, Dec. 1, 2005, pp. 10306-10309, XP055107481, ISSN: 0021-8561, DOI: 10.1021/jf058111a.
Pliskova, M., et al., Effects of silymarin flavonolignans and synthetic silybin derivatives on estrogen and aryl hydrocarbon receptor activation, Toxicology, Limerick, IR, vol. 215, No. 1-2, Nov. 5, 2005, pp. 80-89 XP027602750, ISSN: 0300-483X.
Madeleine, Picq, et al., Pentasubstituted quercetin analogs as selective inhibitors of particulate 3, 5-cyclic-AMP phosphodiesterase from rat brain, Journal of Medicinal Chemistry, vol. 25, No. 10, Oct. 1, 1982, pp. 1192-1198, XP055107500, ISSN: 0022-2623, DOI: 10.1021/jm00352a019.

Database CAPLUS—Jayashree, B.S., et al., Synthesis of substituted 3-hydroxy flavones for antioxidant and antimicrobial activity, XP002721712, retrieved from STN Database accession No. 2009:58730.
Extended European Search Report in Patent Application No. PCT/US2011/045526 dated Mar. 26, 2014.
Belguise et al., Cancer Res, 67:11742-11750 (2007). "Green Tea Polyphenols Reverse Cooperation between c-Rel and CK2 that Induces the Aryl Hydrocarbon Receptor, Slug, and an Invasive Phenotype."
Chen et al., Carcinogenesis, 19(9):1631-1639 (1998). "Aryl hydrocarbon receptor-mediated antiestrogenic and antitumorigenic activity of diindolylmethane."
Currier et al., Toxicologic Pathology, 33:726-737 (2005). "Oncogenic Signaling Pathways Activated in DMBA-Induced Mouse Mammary Tumors."
Davis et al., Toxicology and Applied Pharmacology, 188:42-49 (2003). "The aryl hydrocarbon receptor antagonist, 3'methoxy-4' nitroflavone, attenuates 2,3,7,8-tetrachlorodibenzo-p-dioxin-dependent regulation of growth factor signaling and apoptosis in the MCF-10A cell line."
Denison et al., Annu. Rev. Pharmacol. Toxociol., 43:309-334 (2003). "Activation of the Aryl Hydrocarbon Receptor by Structurally Diverse Exogenous and Endogeous Chemicals."
Edwards et al., Journal of the National Cancer Institute, 97(19):1407-1427 (2005). "Annual Report to the Nation on the Status of Cancer, 1975-2002, Featuring Population-Based Trends in Cancer Treatment."
Esser et al., Trends in Immunology, 30(9):447-454 (2009). "The aryl hydrocarbon receptor in immunity."
Fukuda et al., Journal of Bioscience and Bioengineering, 107(3):296-300 (2009). "Structure-activity relationships of anthraquinones on the suppression of DNA-binding activity of the aryl hydrocarbon receptor induced by 2,3,7,8-tetrachlorodibenzo-p-dioxin."
Gramatzki et al., Oncogene, 28:2593-2605 (2009). "Aryl hydrocarbon receptor inhibition downregulates the TGF-β/Smad pathway in human glioblastoma cells."
Hahn et al., Biochemical Pharmacology, 77:485-497 (2009). "Regulation of constitutive and inducible AHR signaling: Complex interactions involving the AHR repressor."
Harris et al., The New England Journal of Medicine, 327(5):319-328 (1992). "Breast Cancer (First of Three Parts)."
Henry et al., Molecular Pharmacology, 55:716-725 (1999). "Flavone Antagonists Bind Competitively with 2,3,7,8-Tetrachlorodibenzo-p-Dioxin (TCDD) to the Aryl Hydrocarbon Receptor But Inhibit Nuclear Uptake and Transformation."
Hestermann et al., Molecular and Cellular Biology, 23(21):7920-7925 (2003). "Agonist and Chemopreventative Ligands Induce Differential Transcriptional Cofactor Recruitment by Aryl Hydrocarbon Receptor."
Hu et al., Molecular Pharmacology, 71(6):1475-1486 (2007). "Induction of Cyp1a1 is a Nonspecific Biomarker of Aryl Hydrocarbon Receptor Activation: Results of Large Scale Screening of Pharmaceuticals and Toxicants in Vivo and in Vitro."
Kavanagh et al., Journal of Cellular Biochemistry, 82:387-398 (2001). "Green Tea Extracts Decrease Carcinogen-Induced Mammary Tumor Burden in Rats and Rate of Breast Cancer Cell Proliferation in Culture."
Kim et al., Oncogene, 19:5498-5506 (2000). "The RelA NF-κB subunit and the aryl hydrocarbon receptor (AhR) cooperate to transactivate the c-myc promoter in mammary cells."
Kronenberg et al., Nucleic Acids Research, 28(12):2286-2291 (2000). "An aryl hydrocarbon receptor conformation acts as the functional core of nuclear dioxin signaling."
Lawrence et al., Blood, 112:1158-1165 (2008). "Activation of the aryl hydrocarbon receptor is essential for mediating the anti-inflammatory effects of a novel low-molecular-weight compound."
Lu et al., Biochemical Pharmacology, 51:1077-1087 (1996). "Substituted Flavones as Aryl Hydrocarbon (Ah) Receptor Agonists and Antagonists."
Matikainen, et al., Endocrinology, 143(2):615-620 (2002). "Ligand Activation of the Aromatic Hydrocarbon Receptor Transcription Factor Drives Bax-Dependent Apoptosis in Developing Fetal Ovarian Germ Cells."

(56) References Cited

OTHER PUBLICATIONS

Matsuoka-Kawano et al., Chemico-Biological Interactions, 185:33-41 (2010). "TSU-16, (Z)-3-[(2,4-dimethylpyrrol-5-yl)methylidenyl]-2-indoline, is a potent activator of aryl hydrocarbon receptor and increases CYP1A1 and CYP1A2 expression in human hepatocytes."
McDougal et al., Cancer Letters, 120:53-63 (1997). "Inhibition of 7,12-dimethylbenz[a]anthracene-induced rat mammary tumor growth by aryl hydrocarbon receptor agonists."
Min et al., Journal of Cellular Biochemistry, 104:733-744 (2008). "NF-κB and Epithelial to Mesenchymal Transition of Cancer."
Morales et al., Chem Res Toxicol., 21(2):472-482 Author Manuscript (2008). "Characterization of the Antiallergic Drugs 3-[2-(2-Phenylethyl) benzoimidazole-4-yl]-3-hydroxypropanoic Acid and Ethyl 3-Hydroxy-3-[2-(2-phenylethyl)benzoimidazol-4-yl]propanoate as Full Aryl Hydrocarbon Receptor Agonists."
Murray et al., Journal of Cellular Biochemistry, 95:875-884 (2005). "Increased Expression of MDM2, Cyclin D1, and p27Kip1 in Carcinogen-Induced Rat Mammary Tumors."
Murray et al., Breast Cancer Research, 8:R17 (2006). "Growth of a human mammary tumor cell line is blocked by galangin, a naturally occurring bioflavonoid, and is accompanied by down-regulation of cyclins D3, E, and A."
Murray et al., Molecular Pharmacology, 77(2):247-254 (2010). "Evidence for Ligand-Mediated Selective Modulation of Aryl Hydrocarbon Receptor Activity."
Murray et al., Chem Res Toxicol., 23(5):955-966 Author Manuscript (2010). "Development of a Selective Modulator of Aryl Hydrocarbon (Ah) Receptor Activity that Exhibits Anti-Inflammatory Properties."
Narasimhan, ART beCAUSE Breast Cancer Foundation, News and Update, Feb. 2009. "The Role of an Environmental Chemical Receptor, the Aryl Hydrocarbon Receptor, in Breast Cancer Cell Growth and Invasion."
Prud'Homme et al., PLoS One, 5(11):e13831 (2010). "Breast Cancer Stem-Like Cells Are Inhibited by a Non-Toxic Aryl Hydrocarbon Receptor Agonist."
Rannug et al., The Journal of Biological Chemistry, 262(32):15422-15427 (1987). "Certain Photooxidized Derivatives of Tryptophan Bind with Very High Affinity to the Ah Receptor and Are Likely to be Endogenous Signal Substances."
Safe, Toxicology Letters, 120:1-7 (2001). "Molecular biology of the Ah receptor and its role in carcinogenesis."
Sanchez et al., Journal of Biomedicine and Biotechnology, Article 505694 (2010). "The Unexpected Role for the Aryl Hydrocarbon Receptor on Susceptibility to Experimental Toxoplasmosis."
Schlezinger et al., Biol Chem., 387:1175-1187 (2006). "A role for the aryl hydrocarbon receptor in mammary gland tumorigenesis."
SEER Stat Fact Sheets: Breast, Webpage, accessed Aug. 9, 2013 at http://seer.cancer.gov/statfacts/html/breast.html.
Shin et al., Cancer Res, 66:2570-2575 (2006). "7,12-Dimethylbenz(a)Anthracene Treatment of a c-rel Mouse Mammary Tumor Cell Line Induces Epithelial to Mesenchymal Transition via Activation of Nuclear Factor-κB."
Song et al., PNAS, 99(23):14694-14699 (2002). "A ligand for the aryl hydrocarbon receptor isolated from lung."
Trombino et al., Breast Cancer Research and Treatment, 63:117-131 (2000). "Expression of the aryl hydrocarbon receptor/transcription factor (AhR) and AhR-regulated CYP1 gene transcripts in a rat model of mammary tumorigenesis."
Wingo et al., CA Cancer J Clin, 45:8-30 (1995). "Cancer Statistics, 1995".
Yang et al., Oncogene, 24:7869-7881 (2005). "The aryl hydrocarbon receptor constitutively represses c-myc transcription in human mammary tumor cells."
Yang et al., Journal of Cellular Biochemistry, 104:402-417 (2008). "Constitutive Regulation of CYP1B1 by the Aryl Hydrocarbon Receptor (AhR) in Pre-Malignant and Malignant Mammary Tissue."
Yoshinari et al., Biochemical Pharmacology, 76:139-145 (2008). "Omeprazole transactivates human CYP1A1 and CYP1A2 expression through the common regulatory region containing multiple xenobiotic-responsive elements."
Zhang et al., Endocrine-Related Cancer, 16:835-844 (2009). "The aryl hydrocarbon receptor as a target for estrogen receptor-negative breast cancer chemotherapy."
Lee et al., "3',4'-dimethoxyflavone as an Aryl Hydrocarbon Receptor Antagonist in Human Breast Cancer Cells", Toxicological Sciences 58(2):235-242 (2000).
Zhang et al., "Flavonoids as Aryl Hydrocarbon Receptor Agonists/Antagonists: Effects of Structure and Cell Context", Environmental Health Perspectives 111(16):1877-1882 (2003).
Jayashree et al., "Synthesis of Substituted 3-Hydroxy Flavones for Antioxidant and Antimicrobial Activity", Pharmacologyonline 3:586-595 (2008).
Boitano et al., "Aryl Hydrocarbon Receptor Antagonists Promote the Expansion of Human Hematopoietic Stem Cells", Science 329:1345-1348 (2010).
Dorwald F., "Side Reactions in Organic Synthesis: A Guide to Successful Synthesis Design", Wiley VCH Verlag GmbH & Co. KGaA 1-15 (2005).
Fang et al., "In vivo effects of the pure aryl hydrocarbon receptor antagonist GNF-351 after oral administration are limited to the gastrointestinal tract", British Journal of Pharmaoclogy 171:1735-1746 (2014).
Lippard S., "The art of chemistry", Nature 416:587 (2002).
Murray et al., "Antagonism of Aryl Hydrocarbon Receptor Signaling by 6,2',4'-Trimethoxyflavone", The Journal of Pharmacology and Experimental Therapeutics 332(1):135-144 (2010).
National Center for Biotechnology Information. PubChem Substance Database. SID 50718513. Web Jul. 6, 2016 <https://pubchem.ncbi.nlm.gov/substance/50718513>.
Palermo et al., "Identification of Potential Aryl Hydrocarbon Receptor Antagonists in Green Tea", Chemical Research in Toxicology 16:865-872 (2003).
Parmar et al., "Anti-Invasive Activity of Alkaloids and Polyphenolics in Vitro", Bioorganic & Medicinal Chemistry 5(8):1609-1619 (1997).
Revel et al., "Resveratrol, a natural aryl hydrocarbon receptor antagonist, protects sperm from DNA damage and apoptosis caused by benzo(a)pyrene", Reproductive Toxicology 15:479-486 (2001).
STN Registry No. 819828-98-1 "2-[[2-(5-bromo-2-furanyl)-4-oxo-4H-1-benzopyran-3-yl]oxy]-N-[3-(trifluoromethyl)phenyl]-acetamide". STN Database. Jan. 19, 2017. One Page.
STN Registry No. 819829-46-4. "2-[[2-(5-bromo-2-furanyl)-4-oxo-4H-1-benzopyran-3-yl]oxy]-N ,N-diethyl acetamide", STN Database (2005).
Dormeyer et al., "Rational design of anticytoadherence inhibitors for Plasmodium falciparum based on the crystal structure of human intercellular adhesion molecule 1." Antimicrob Agents Chemother. 50(2): 742-30 (2006).
Kidd "986. Potential bronchodilators in the flavonoid series." Journal of the Chemical Society (Resumed) 5121-5125 (1962).
Lin et al., "Chalcones and flavonoids as anti-tuberculosis agents." Bioorg Med Chem 10(8): 2795-802 (2002).

\* cited by examiner

SEQUENCE LISTING

<160> NUMBER OF SEQ ID NOS: 2

<210> SEQ ID NO 1
<211> LENGTH: 848
<212> TYPE: PRT
<213> ORGANISM: Homo sapiens

<400> SEQUENCE: 1

```
Met Asn Ser Ser Ser Ala Asn Ile Thr Tyr Ala Ser Arg Lys Arg Arg
1               5                   10                  15

Lys Pro Val Gln Lys Thr Val Lys Pro Ile Pro Ala Glu Gly Ile Lys
            20                  25                  30

Ser Asn Pro Ser Lys Arg His Arg Asp Arg Leu Asn Thr Glu Leu Asp
        35                  40                  45

Arg Leu Ala Ser Leu Leu Pro Phe Pro Gln Asp Val Ile Asn Lys Leu
    50                  55                  60

Asp Lys Leu Ser Val Leu Arg Leu Ser Val Ser Tyr Leu Arg Ala Lys
65                  70                  75                  80

Ser Phe Phe Asp Val Ala Leu Lys Ser Ser Pro Thr Glu Arg Asn Gly
                85                  90                  95

Gly Gln Asp Asn Cys Arg Ala Ala Asn Phe Arg Glu Gly Leu Asn Leu
                100                 105                 110

Gln Glu Gly Glu Phe Leu Leu Gln Ala Leu Asn Gly Phe Val Leu Val
            115                 120                 125

Val Thr Thr Asp Ala Leu Val Phe Tyr Ala Ser Ser Thr Ile Gln Asp
    130                 135                 140

Tyr Leu Gly Phe Gln Gln Ser Asp Val Ile His Gln Ser Val Tyr Glu
145                 150                 155                 160

Leu Ile His Thr Glu Asp Arg Ala Glu Phe Gln Arg Gln Leu His Trp
                165                 170                 175

Ala Leu Asn Pro Ser Gln Cys Thr Glu Ser Gly Gln Gly Ile Glu Glu
                180                 185                 190

Ala Thr Gly Leu Pro Gln Thr Val Val Cys Tyr Asn Pro Asp Gln Ile
            195                 200                 205

Pro Pro Glu Asn Ser Pro Leu Met Glu Arg Cys Phe Ile Cys Arg Leu
    210                 215                 220

Arg Cys Leu Leu Asp Asn Ser Ser Gly Phe Leu Ala Met Asn Phe Gln
225                 230                 235                 240

Gly Lys Leu Lys Tyr Leu His Gly Gln Lys Lys Gly Lys Asp Gly
                245                 250                 255

Ser Ile Leu Pro Pro Gln Leu Ala Leu Phe Ala Ile Ala Thr Pro Leu
            260                 265                 270

Gln Pro Pro Ser Ile Leu Glu Ile Arg Thr Lys Asn Phe Ile Phe Arg
    275                 280                 285

Thr His Lys His Lys Leu Asp Phe Thr Pro Ile Gly Cys Asp Ala Lys Gly
290                 295                 300

Arg Ile Val Leu Gly Tyr Thr Glu Ala Glu Leu Cys Thr Arg Gly Ser
305                 310                 315                 320

Gly Tyr Gln Phe Ile His Ala Ala Asp Met Leu Tyr Cys Ala Glu Ser
                325                 330                 335

His Ile Arg Met Ile Lys Thr Gly Glu Ser Gly Met Ile Val Phe Arg
                340                 345                 350

Leu Leu Thr Lys Asn Asn Arg Trp Thr Trp Val Gln Ser Asn Ala Arg
            355                 360                 365
```

```
Leu Leu Tyr Lys Asn Gly Arg Pro Asp Tyr Ile Ile Val Thr Gln Arg
        370                 375                 380

Pro Leu Thr Asp Glu Glu Gly Thr Glu His Leu Arg Lys Arg Asn Thr
385                 390                 395                 400

Lys Leu Pro Phe Met Phe Thr Thr Gly Glu Ala Val Leu Tyr Glu Ala
                405                 410                 415

Thr Asn Pro Phe Pro Ala Ile Met Asp Pro Leu Pro Leu Arg Thr Lys
            420                 425                 430

Asn Gly Thr Ser Gly Lys Asp Ser Ala Thr Thr Ser Thr Leu Ser Lys
        435                 440                 445

Asp Ser Leu Asn Pro Ser Ser Leu Leu Ala Ala Met Met Gln Gln Asp
    450                 455                 460

Glu Ser Ile Tyr Leu Tyr Pro Ala Ser Ser Thr Ser Ser Thr Ala Pro
465                 470                 475                 480

Phe Glu Asn Asn Phe Phe Asn Glu Ser Met Asn Glu Cys Arg Asn Trp
                485                 490                 495

Gln Asp Asn Thr Ala Pro Met Gly Asn Asp Thr Ile Leu Lys His Glu
            500                 505                 510

Gln Ile Asp Gln Pro Gln Asp Val Asn Ser Phe Ala Gly Gly His Pro
        515                 520                 525

Gly Leu Phe Gln Asp Ser Lys Asn Ser Asp Leu Tyr Ser Ile Met Lys
    530                 535                 540

Asn Leu Gly Ile Asp Phe Glu Asp Ile Arg His Met Gln Asn Glu Lys
545                 550                 555                 560

Phe Phe Arg Asn Asp Phe Ser Gly Glu Val Asp Phe Arg Asp Ile Asp
                565                 570                 575

Leu Thr Asp Glu Ile Leu Thr Tyr Val Gln Asp Ser Leu Ser Lys Ser
            580                 585                 590

Pro Phe Ile Pro Ser Asp Tyr Gln Gln Gln Gln Ser Leu Ala Leu Asn
        595                 600                 605

Ser Ser Cys Met Val Gln Glu His Leu His Leu Glu Gln Gln Gln Gln
    610                 615                 620

His His Gln Lys Gln Val Val Val Glu Pro Gln Gln Gln Leu Cys Gln
625                 630                 635                 640

Lys Met Lys His Met Gln Val Asn Gly Met Phe Glu Asn Trp Asn Ser
                645                 650                 655

Asn Gln Phe Val Pro Phe Asn Cys Pro Gln Gln Asp Pro Gln Gln Tyr
            660                 665                 670

Asn Val Phe Thr Asp Leu His Gly Ile Ser Gln Glu Phe Pro Tyr Lys
        675                 680                 685

Ser Glu Met Asp Ser Met Pro Tyr Thr Gln Asn Phe Ile Ser Cys Asn
    690                 695                 700

Gln Pro Val Leu Pro Gln His Ser Lys Cys Thr Glu Leu Asp Tyr Pro
705                 710                 715                 720

Met Gly Ser Phe Glu Pro Ser Pro Tyr Pro Thr Thr Ser Ser Leu Glu
                725                 730                 735

Asp Phe Val Thr Cys Leu Gln Leu Pro Glu Asn Gln Lys His Gly Leu
            740                 745                 750

Asn Pro Gln Ser Ala Ile Ile Thr Pro Gln Thr Cys Tyr Ala Gly Ala
        755                 760                 765
```

```
Val Ser Met Tyr Gln Cys Gln Pro Glu Pro Gln His Thr His Val Gly
        770             775             780

Gln Met Gln Tyr Asn Pro Val Leu Pro Gly Gln Gln Ala Phe Leu Asn
785             790             795                         800

Lys Phe Gln Asn Gly Val Leu Asn Glu Thr Tyr Pro Ala Glu Leu Asn
                805             810                 815

Asn Ile Asn Asn Thr Gln Thr Thr Thr His Leu Gln Pro Leu His His
                820             825             830

Pro Ser Glu Ala Arg Pro Phe Pro Asp Leu Thr Ser Ser Gly Phe Leu
            835             840             845

<210> SEQ ID NO 2
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other

<400> SEQUENCE: 2 tngcgtg                                                                 7
```

ARYL HYDROCARBON RECEPTOR (AHR) MODIFIERS AS NOVEL CANCER THERAPEUTICS

CROSS REFERENCE TO RELATED APPLICATIONS

This application is a 35 U.S.C. § 371 National Phase Entry Application of International Application No. PCT/US2011/045056 filed 22 Jul. 2011, which designates the U.S., and which claims benefit under 35 U.S.C. § 119(e) of U.S. Provisional Application Ser. No. 61/368,042 filed on 27 Jul. 2010, the contents of which are incorporated herein by reference in their entireties.

GOVERNMENT SUPPORT

This invention was made with Government Support under Contract Nos. ES011624 and CA134882 awarded by the National Institutes of Health (NIH). The Government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 20, 2013 is named 701586-067982-US_SL.txt and is 8,192 bytes in size.

FIELD OF THE INVENTION

The invention generally relates to compositions and methods for modulating AhR activity.

BACKGROUND

Cancer remains one of the most deadly threats to human health. In the U.S., cancer affects nearly 1.3 million new patients each year, and is the second leading cause of death after heart disease, accounting for approximately 1 in 4 deaths. It is also predicted that cancer may surpass cardiovascular diseases as the number one cause of death within the next decade. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making timely detection and treatment extremely difficult.

In the U.S., the age-adjusted incidence of breast cancer increased ~1% per year between 1940 and 1990 (27, 28) and 0.4%/year between 1987 and 2002 (29), due, in part to increased exposure to environmental carcinogens. Breast cancer is now the second most common cancer (after skin cancer) in women, with 225,000 new U.S. cases and 40,000 breast cancer-related deaths per year. It is estimated that 1 in 8 women born this year will be diagnosed with breast cancer in their lifetime (34). The total number of women diagnosed with breast cancer is likely to grow significantly over the next 20 years as the demographics of the population shift towards an older population (34).

SUMMARY OF THE INVENTION

Described herein are novel agents that modulate AhR activity for use in therapeutic compositions and methods thereof for inhibiting cancer cell proliferation and tumor cell invasion and metastasis. These compositions and methods are based on the inventors' novel discovery that pharmaceutical compositions comprising small molecule compounds of Formula (I) and (II) described herein modulate AhR activity, such as constitutive AhR activity. The inventors have discovered that such small molecules can bind to the AhR and block or inhibit those functions and signaling pathways regulated by the AhR that influence cancer cell growth and proliferation, and tumor cell invasiveness. The inventors have further discovered that the pharmaceutical compositions comprising small molecule compounds of Formula (I) and (II) described herein can act as either AhR inhibitors or non-constitutive AhR agonists, and further provide novel methods and assays to distinguish the types of AhR modulators. Accordingly, provided herein are novel therapeutic pharmaceutical compositions and methods thereof comprising AhR inhibitors or non-constitutive AhR agonists of Formula (I) and (II) for the inhibition of cancer cell growth and parameters that characterize tumor metastasis, such as tumor cell invasiveness.

Accordingly, described herein are novel AhR modulators. In some aspects, described herein are pharmaceutical compositions comprising an aryl hydrocarbon receptor (AhR) modulator of Formula (I):

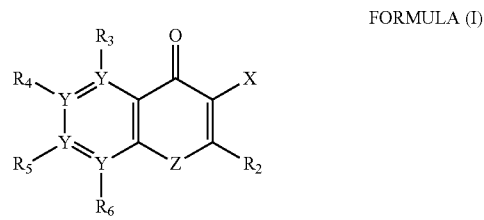

FORMULA (I)

wherein:
Y is C or N;
X is $OR_1$, $NHR_1$, $SR_1$, $CH_2(n)R_1$, halo, or H;
n is 0-6;
Z is O, S, or NH;
$R_1$, and $R_2$ are independently H, alkyl, alkenyl, alkynyl, amino, aminosulfonyl, alkoxy, acyl, aryl, heteroaryl, arylalkyl, cycloalkyl, heteroarylalkyl, heterocyclyl, or haloalkyl, each of which may be optionally substituted;
$R_3$, $R_4$, $R_5$ and $R_6$ are independently absent, H, halo, alkyl, alkenyl, alkynyl, alkoxy, acyl, aryl, heteroaryl, arylalkyl, cycloalkyl, heteroarylalkyl, heterocyclyl, or haloalkyl, each of which may be optionally substituted;
pharmaceutically acceptable salts thereof.

In some embodiments of these aspects and all such aspects described herein, the AhR modulator of Formula (I) is an AhR inhibitor or a non-constitutive AhR agonist. In some such embodiments, the AhR inhibitor is CB7993113 having a chemical structure:

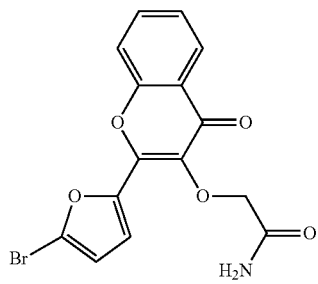 [SMILES: NC(=O)COc1c(-c2ccc(Br)o2)oc2ccccc2c1=O]

In some such embodiments, the non-constitutive AhR agonist is CB7950998 having a chemical structure:

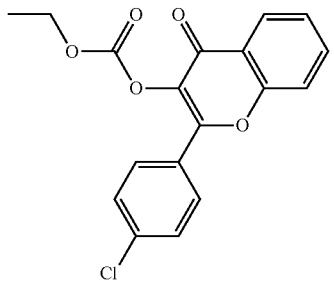 [SMILES: CCOC(=O)Oc1c(-c2ccc(Cl)cc2)oc2ccccc2c1=O]

In some aspects, the pharmaceutical composition comprises an AhR modulator of Formula (Ia):

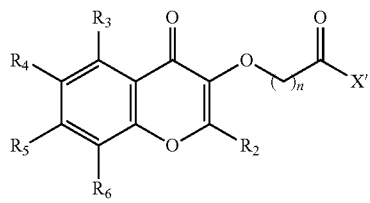

FORMULA (Ia)

wherein:
X' is H, alkyl, aminosulfonyl, alkoxy, amino, acyl, aryl, or heteroaryl, each of which may be optionally substituted;
n is 0-6;
$R_2$ is H, alkyl, acyl, aryl, heteroaryl, arylalkyl, cycloalkyl, heteroarylalkyl, heterocyclyl, or haloalkyl, each of which may be optionally substituted;
$R_3$, $R_4$, $R_5$ and $R_6$ are independently H, alkyl, acyl, halo, aryl, or heteroaryl, each of which may be optionally substituted; and
pharmaceutically acceptable salts thereof.

In some embodiments of the AhR inhibitor of Formula (Ia),
X' is alkyl, alkoxy, amino, or aminosulfonyl;
n is 0 or 1;
$R_2$ is aryl, substituted aryl, heteroaryl, or substituted aryl; and
$R_3$, $R_4$, $R_5$ and $R_6$ are independently H, alkoxy, alkyl, or halo.

In some embodiments of these aspects and all such aspects described herein, the AhR modulator of Formula (Ia) is an AhR inhibitor or a non-constitutive AhR agonist.

In other aspects, provided herein are compositions comprising a compound of Formula (II):

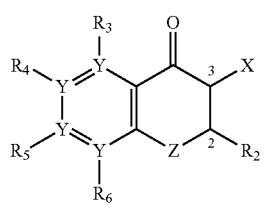

FORMULA (II)

wherein:
Y is C or N;
X is $OR_1$, $NHR_1$, $SR_1$, $CH_2(n)R_1$, halo, or H;
n is 0-6;
Z is O, S, or NH;
$R_1$, and $R_2$ are independently H, alkyl, alkenyl, alkynyl, amino, aminosulfonyl, alkoxy, acyl, aryl, heteroaryl, arylalkyl, cycloalkyl, heteroarylalkyl, heterocyclyl, or haloalkyl, each of which may be optionally substituted;
$R_3$, $R_4$, $R_5$ and $R_6$ are independently absent, H, halo, alkyl, alkenyl, alkynyl, alkoxy, acyl, aryl, heteroaryl, arylalkyl, cycloalkyl, heteroarylalkyl, heterocyclyl, or haloalkyl, each of which may be optionally substituted; and stereoisomers thereof.

In some embodiments of these aspects, the C at position 2 is in the R configuration and the C at position 3 is in the S configuration. In some embodiments of these aspects, the C at position 2 is in the S configuration and the C at position 3 is in the R configuration. In some embodiments of these aspects, the C at position 2 is in the R configuration and the C at position 3 is in the R configuration. In some embodiments of these aspects, the C at position 2 is in the S configuration and the C at position 3 is in the S configuration.

In some embodiments of these aspects, the compound is CMLD-2166 having a chemical structure:

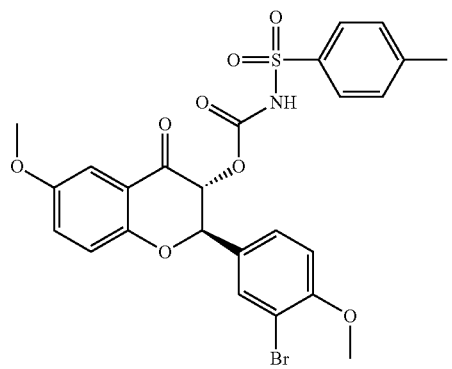 [SMILES: COc1ccc2c(c1)C(=O)[C@H](OC(=O)NS(=O)(=O)c1ccc(C)cc1)[C@@H](c1ccc(OC)c(Br)c1)O2]

In some aspects, provided herein are compositions comprising a compound of formula (IIa):

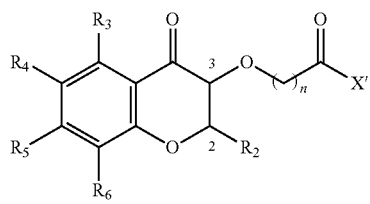

FORMULA (IIa)

wherein:
X' is H, alkyl, aminosulfonyl, alkoxy, acyl, aryl, or heteroaryl, each of which may be optionally substituted;
n is 0-6;
$R_2$ is H, alkyl, acyl, aryl, heteroaryl, arylalkyl, cycloalkyl, heteroarylalkyl, heterocyclyl, or haloalkyl, each of which may be optionally substituted;
$R_3$, $R_4$, $R_5$ and $R_6$ are independently H, alkyl, acyl, halo, aryl, or heteroaryl, each of which may be optionally substituted; and stereoisomers thereof.

In some embodiments of these aspects and all such aspects described herein,

X' is alkyl, alkoxy, aminosulfonyl;

n is 0 or 1;

$R_2$ is aryl, substituted aryl, heteroaryl, or substituted aryl; and $R_3$, $R_4$, $R_5$ and $R_6$ are independently H, alkoxy, alkyl, or halo.

In some aspects, provided herein are pharmaceutical compositions comprising an aryl hydrocarbon receptor (AhR) modulator of Formula (II):

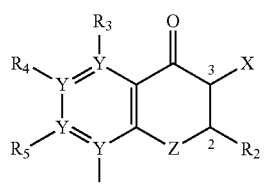

FORMULA (II)

wherein:

Y is C or N;

X is $OR_1$, $NHR_1$, $SR_1$, $CH_2(n)R_1$, halo, or H;

n is 0-6;

Z is O, S, or NH;

$R_1$, and $R_2$ are independently H, alkyl, alkenyl, alkynyl, amino, aminosulfonyl, alkoxy, acyl, aryl, heteroaryl, arylalkyl, cycloalkyl, heteroarylalkyl, heterocyclyl, or haloalkyl, each of which may be optionally substituted;

$R_3$, $R_4$, $R_5$ and $R_6$ are independently absent, H, halo, alkyl, alkenyl, alkynyl, alkoxy, acyl, aryl, heteroaryl, arylalkyl, cycloalkyl, heteroarylalkyl, heterocyclyl, or haloalkyl, each of which may be optionally substituted;

stereoisomers thereof; and pharmaceutically acceptable salts thereof.

In some embodiments of these aspects and all such aspects described herein, the stereoisomers thereof comprise the C at position 2 in an R configuration and the C at position 3 in an S configuration. In some embodiments of the aspect, the stereoisomers thereof comprise the C at position 2 in an S configuration and the C at position 3 in an R configuration. In some embodiments of the aspect, the stereoisomers thereof comprise the C at position 2 in an R configuration and the C at position 3 in an R configuration. In some embodiments of the aspect, the stereoisomers thereof comprise the C at position 2 in an S configuration and the C at position 3 in an S configuration.

In some embodiments of these aspects and all such aspects described herein, the AhR modulator of Formula (II) is an AhR inhibitor or a non-constitutive AhR agonist.

In some embodiments of these aspects, the AhR modulator of Formula (II) is CMLD-2166 having a chemical structure:

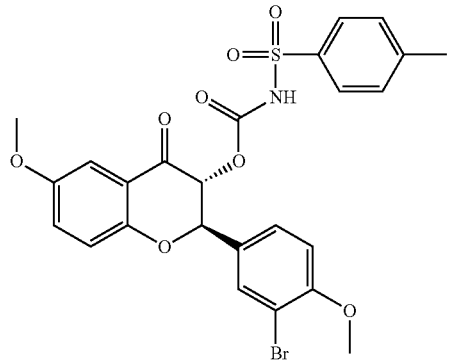

CMLD-2166

In some aspects, provided herein are pharmaceutical compositions comprising an aryl hydrocarbon receptor (AhR) modulator of Formula (IIa):

FORMULA (IIa)

wherein:

X' is H, alkyl, aminosulfonyl, alkoxy, acyl, aryl, or heteroaryl, each of which may be optionally substituted;

n is 0-6;

$R_2$ is H, alkyl, acyl, aryl, heteroaryl, arylalkyl, cycloalkyl, heteroarylalkyl, heterocyclyl, or haloalkyl, each of which may be optionally substituted;

$R_3$, $R_4$, $R_5$ and $R_6$ are independently H, alkyl, acyl, halo, aryl, or heteroaryl, each of which may be optionally substituted;

stereoisomers thereof; and pharmaceutically acceptable salts thereof.

In some embodiments of these aspects of the AhR modulator of Formula (IIa),

X' is alkyl, alkoxy, aminosulfonyl;

n is 0 or 1;

$R_2$ is aryl, substituted aryl, heteroaryl, or substituted aryl; and $R_3$, $R_4$, $R_5$ and $R_6$ are independently H, alkoxy, alkyl, or halo.

In some embodiments of these aspects and all such aspects described herein, the AhR modulator of Formula (IIa) is an AhR inhibitor or a non-constitutive AhR agonist.

In some aspects, described herein are methods of modulating constitutive AhR activity in a subject in need thereof. Such methods comprise administering to a subject having constitutive AhR activity a therapeutically effective amount of any of the pharmaceutical compositions comprising an AhR modulator, such as an AhR inhibitor (e.g., CB7993113 or CMLD-2166), or a non-constitutive AhR agonist (e.g., CB7950998) of Formulas (I), (Ia), (II), or (IIa) described herein. In some embodiments of these aspects and all such aspects described herein, the methods further comprise the step of selecting the subject having constitutive AhR activity.

In other aspects, described herein are methods of treating a cancer or a cancerous condition by modulating AhR activity. Such methods comprise administering to a subject having a cancer or cancerous condition a therapeutically effective amount of any of the pharmaceutical compositions comprising an AhR modulator, such as an AhR inhibitor (e.g., CB7993113 or CMLD-2166), or a non-constitutive AhR agonist (e.g., CB7950998) of Formulas (I), (Ia), (II), or (IIa) described herein.

In some aspects, described herein are methods of inhibiting tumor cell invasiveness in a subject having a cancer, a cancerous condition, or a tumor. Such methods comprise administering to a subject having a cancer or a tumor a therapeutically effective amount of any of the pharmaceutical compositions comprising an AhR modulator, such as an AhR inhibitor (e.g., CB7993113 or CMLD-2166), or a non-constitutive AhR agonist (e.g., CB7950998) of Formulas (I), (Ia), (II), or (IIa) described herein.

In some embodiments of these aspects and all such aspects described herein, the methods further comprise the step of selecting the subject having a cancer, a cancerous condition, or a tumor.

In some embodiments of these methods, the cancer is a breast cancer, squamous cell cancer, lung cancer, a cancer of the peritoneum, a hepatocellular cancer, a gastric cancer, a pancreatic cancer, a glioblastoma, a cervical cancer, an ovarian cancer, a liver cancer, a bladder cancer, a hepatoma, a colon cancer, a colorectal cancer, an endometrial or uterine carcinoma, a salivary gland carcinoma, a kidney or renal cancer, a prostate cancer, a vulval cancer, a thyroid cancer, a head and neck cancer, a B-cell lymphoma, a chronic lymphocytic leukemia (CLL); an acute lymphoblastic leukemia (ALL), a Hairy cell leukemia, or a chronic myeloblastic leukemia. In some such embodiments, the cancer is a breast cancer.

Some embodiments of these methods can further comprise administration or treatment with one or more additional anti-cancer therapies. In some such embodiments, the additional anti-cancer therapy comprises surgery, radiation therapy, biotherapy, immunotherapy, chemotherapy, or any combination thereof.

Some embodiments of these methods can further comprise administration or treatment with one or more anti-cancer therapeutic agents. In some such embodiments, the anti-cancer therapeutic agent is a chemotherapeutic agent, a growth inhibitor agent, an anti-angiogenesis agent, a cytotoxic agent, an anti-hormonal agent, a prodrug, or a cytokine.

Also provided herein, in other aspects, are pharmaceutical compositions comprising an AhR modulator, such as an AhR inhibitor (e.g., CB7993113 or CMLD-2166), or a non-constitutive AhR agonist (e.g., CB7950998) of Formulas (I), (Ia), (II), or (IIa), for use in modulating constitutive AhR activity in a subject in need thereof.

In some aspects, pharmaceutical compositions comprising an AhR modulator, such as an AhR inhibitor (e.g., CB7993113 or CMLD-2166), or a non-constitutive AhR agonist (e.g., CB7950998) of Formulas (I), (Ia), (II), or (IIa), are provided for use in treating a cancer or a cancerous condition by modulating AhR activity.

In some aspects, pharmaceutical compositions comprising an AhR modulator, such as an AhR inhibitor (e.g., CB7993113 or CMLD-2166), or a non-constitutive AhR agonist (e.g., CB7950998) of Formulas (I), (Ia), (II), or (IIa), are provided for use in inhibiting tumor cell invasiveness in a subject having a cancer, a cancerous condition, or a tumor.

In some embodiments of these aspects and all such aspects described herein, the use further comprises the step of selecting the subject having a cancer, a cancerous condition, or a tumor. In some such embodiments, the cancer is a breast cancer, squamous cell cancer, lung cancer, a cancer of the peritoneum, a hepatocellular cancer, a gastric cancer, a pancreatic cancer, a glioblastoma, a cervical cancer, an ovarian cancer, a liver cancer, a bladder cancer, a hepatoma, a colon cancer, a colorectal cancer, an endometrial or uterine carcinoma, a salivary gland carcinoma, a kidney or renal cancer, a prostate cancer, a vulval cancer, a thyroid cancer, a head and neck cancer, a B-cell lymphoma, a chronic lymphocytic leukemia (CLL); an acute lymphoblastic leukemia (ALL), a Hairy cell leukemia, or a chronic myeloblastic leukemia. In some such embodiments, the cancer is a breast cancer.

In some embodiments of these aspects and all such aspects described herein, the use further comprises one or more additional anti-cancer therapies. In some such embodiments, the additional anti-cancer therapy comprises surgery, radiation therapy, biotherapy, immunotherapy, or chemotherapy.

In some embodiments of these aspects and all such aspects described herein, the use further comprises one or more anti-cancer therapeutic agents. In some such embodiments, the anti-cancer therapeutic agent is a chemotherapeutic agent, a growth inhibitor agent, an anti-angiogenesis agent, a cytotoxic agent, an anti-hormonal agent, a prodrug, or a cytokine.

Other aspects described herein provide novel screening methods for identifying an AhR modulator, such as an AhR inhibitor or a non-constitutive AhR agonist, of Formula (I), (Ia), (II), or (IIa). In one such aspect, a screening method of identifying an AhR modulator is provided, the method comprising:

a. contacting a cell comprising a sequence encoding an AhR receptor operably linked to a sequence encoding a reporter molecule with a strong AhR activator, such that expression of the reporter molecule by the cell indicates that the AhR receptor is activated by the strong AhR activator b. contacting the cell of (a) with a test agent, such that a decrease in the expression of the reporter molecule in the presence of the test agent indicates that the test agent is an AhR modulator; and c. contacting a cell comprising a sequence encoding an AhR receptor operably linked to a sequence encoding a reporter molecule with the AhR modulator in the absence of a strong AhR activator, wherein lack of expression of the reporter molecule by the cell indicates that the AhR modulator is an AhR inhibitor, and wherein expression of the reporter molecule by the cell indicates that the AhR modulator is a partial AhR agonist.

In some embodiments of the aspect and all such aspects described herein, the screening method further comprises contacting the partial AhR agonist with a tumor activity assay system comprising: (i) a tumor cell and (ii) a mixture comprising one or more extracellular matrix components, wherein inhibition of tumor activity by the partial AhR agonist indicates that the partial AhR agonist is a non-constitutive AhR agonist, and wherein an increase in tumor activity by the partial AhR agonist indicates that the partial AhR agonist is a constitutive AhR agonist.

In some embodiments of the screening methods described herein, the reporter is a fluorescent protein, such as GFP (green fluorescent protein) or RFP (red fluorescent protein).

In some embodiments of the screening methods, the strong AhR activator is TCDD or BNF.

In some embodiments of the screening methods, the tumor activity being measured in the tumor activity assay system is tumor cell proliferation or tumor cell invasiveness. In some embodiments of the screening methods, the tumor cell is a human mammary tumor cell. In some embodiments of the screening methods, the mixture comprising one or more extracellular matrix components is Matrigel. In some such embodiments, the one or more extracellular matrix components comprises laminin and collagen.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "aryl hydrocarbon receptor (AhR) modulator" refers to an agent that causes or facilitates a qualitative or quantitative change, alteration, or modification in one or more processes, mechanisms, effects, responses, functions, activities or pathways mediated by the AhR receptor. Such changes mediated by an AhR modulator, such as an inhibitor or a non-constitutive agonist of the AhR described herein, can refer to a decrease or an increase in the activity or function of the AhR, such as a decrease in, inhibition of, or diversion of, constitutive activity of the AhR.

The terms "inhibitor of AhR" or "AhR inhibitor" refers to an agent or compound, that inhibits one or more AhR signaling and downstream effector pathways, including constitutive AhR signaling, as those terms are used herein. Thus, the term AhR inhibitor refers to an agent that inhibits expression of the AhR polypeptide or polynucleotide encoding the AhR, or one that binds to, partially or totally blocks stimulation, decreases, prevents, delays activation, inactivates, desensitizes, or down regulates the activity of the AhR polypeptide or polynucleotide encoding the AhR. Such AhR inhibitors can e.g., inhibit AhR expression, e.g., AhR translation, post-translational processing of the AhR, stability, degradation, or nuclear or cytoplasmic localization of the AhR polypeptide, or transcription, post transcriptional processing, stability or degradation of a polynucleotide encoding the AhR, or bind to, partially or totally block stimulation, DNA binding, or transcription factor activity of the AhR. An AhR inhibitor can act directly or indirectly.

An "AhR antagonist" refers to an AhR inhibitor that does not provoke a biological response itself upon specifically binding to the AhR polypeptide or polynucleotide encoding the AhR, but blocks or dampens agonist-mediated or ligand-mediated responses, i.e., an AhR antagonist can bind but does not activate the AhR polypeptide or polynucleotide encoding the AhR, and the binding disrupts the interaction, displaces an AhR agonist, and/or inhibits the function of an AhR agonist. Thus, as used herein, an AhR antagonist does not function as an inducer of AhR activity when bound to the AhR, i.e., they function as pure AhR inhibitors.

As used herein, the terms "non-constitutive agonist of AhR", "non-constitutive AhR agonist", "non-constitutive activator of AhR," or "non-constitutive AhR activator" refer to an agent or compound that binds to the AhR and hyper-activates or diverts constitutive AhR signaling and downstream effector pathways, as those terms are used herein. Such non-constitutive AhR agonists of can increase expression of the AhR polypeptide or polynucleotide encoding the AhR, or bind to the AhR, and partially or totally divert constitutive AhR signaling and downstream activity, such as cancer cell growth and tumor invasive properties. Accordingly, a non-constitutive AhR agonist of can divert constitutive AhR signaling by about at least 10% or more, at least 20% or more, at least 30% or more, at least 40% or more, at least 50% or more, at least 60% or more, at least 70% or more, at least 80% or more, at least 90% or more, at least 95% or more, or at least 100% or completely in comparison to a reference or control level in the absence of the non-constitutive AhR agonist.

The AhR agonists, AhR non-constitutive agonists, AhR inhibitors, and AhR antagonists described herein can be naturally occurring and synthetic ligands, antagonists, agonists, small chemical molecules, antibodies or antigen-binding fragments thereof, inhibitory RNA molecules (i.e., siRNA or antisense RNA) and the like. Assays to identify AhR agonists, AhR non-constitutive agonists, AhR inhibitors, and AhR antagonists include, e.g., applying putative AhR modulator compounds to cells, in the presence or absence of a polypeptide or polynucleotide and then determining the functional effects on a polypeptide or polynucleotide.

The terms "subject" and "individual" are used interchangeably herein, and refer to an animal, for example a human, recipient of the small molecule AhR modulators of Formula (I) or Formula (II) described herein. For treatment of those disease states which are specific for a specific animal, such as a human subject, the term "subject" refers to that specific animal. The terms 'non-human animals' and 'non-human mammals' are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish.

The terms "cancer" and "cancerous" refer to or describe the physiological condition in mammals that is typically characterized by unregulated cell growth or proliferation, which interferes with the normal functioning of the bodily organs and systems. Cancers which migrate from their original location and seed vital organs can eventually lead to the death of the subject through the functional deterioration of the affected organs. Hematopoietic cancers, such as leukemia, are able to out-compete the normal hematopoietic compartments in a subject, thereby leading to hematopoietic failure (in the form of anemia, thrombocytopenia and neutropenia) ultimately causing death. Included in this definition are benign and malignant cancers, as well as dormant tumors or micrometastatses.

The term "anti-cancer therapy" refers to a therapy or therapeutic agent useful in treating cancer. Examples of anti-cancer therapeutic agents include, but are limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin™), anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the embodiments described herein.

The term "screening" as used herein refers to the use of cells and tissues in the laboratory, and methods thereof, to identify agents with a specific function, e.g., a modulating activity. In some embodiments, described herein are screening methods to identify agents (e.g., compounds or drugs) that inhibit or otherwise modulate AhR activity.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and the include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

BRIEF DESCRIPTION OF THE FIGURES

FIG. 4A shows H1G1 cells expressing an AhR-driven GFP reporter construct and treated with candidate AhR modifiers alone (dark line) or together with BNF, a known AhR agonist (light line). A dark circle identifies an AhR inhibitor while the light circle indicates an agonist. FIG. 4B shows data from the non-toxic compound identified in "A," which was titered in the presence of BNF to calculate the $IC_{50}$. Over 4,000 compounds were screened in this semi-automated assay.

FIG. 5A shows data from malignant BP1 and immortalized MCF-10F cells that were transiently transfected with AhR-responsive pGudLuc and treated with vehicle (DMSO), CH2231

91, or 2166. FIG. 5B shows data from BP1 and MCF-10F cells that were grown for 18 hrs in the presence of DMSO, CH2231 91, or 2166 and 3H-thymidine incorporation determined. *p<0.05.

FIG. 8A shows data from C57BL/6 mice (6/group) that were injected i.p. on day −1 and day 0 with vehicle (oil) or 50 mg/kg CB7993113. Mice then were injected with 50 mg/kg DMBA. Mice were sacrificed 48 hours later. Bone marrow hematopoietic cells were expunged from the bone and viable cells counted. Data are presented as the average number of viable white blood cells+SE. p<0.01, *P<0.001, student's t-test. FIG. 8B confirms the data shown in FIG. 8A and further demonstrates that the three subpopulations of bone marrow cells affected by DMBA are all rescued by treatment with CB7993113. C57BL/6 mice (6/group) were treated as in FIG. 8A. The percentage and number of viable bone marrow pro B cells, pre B cells, and neutrophils were determined 48 hours later by flow cytometry. Data are presented as the average number of viable cells of each subtype+SE. (*p<0.05, **P<0.01, student's t-test).

DETAILED DESCRIPTION

Figure 1:
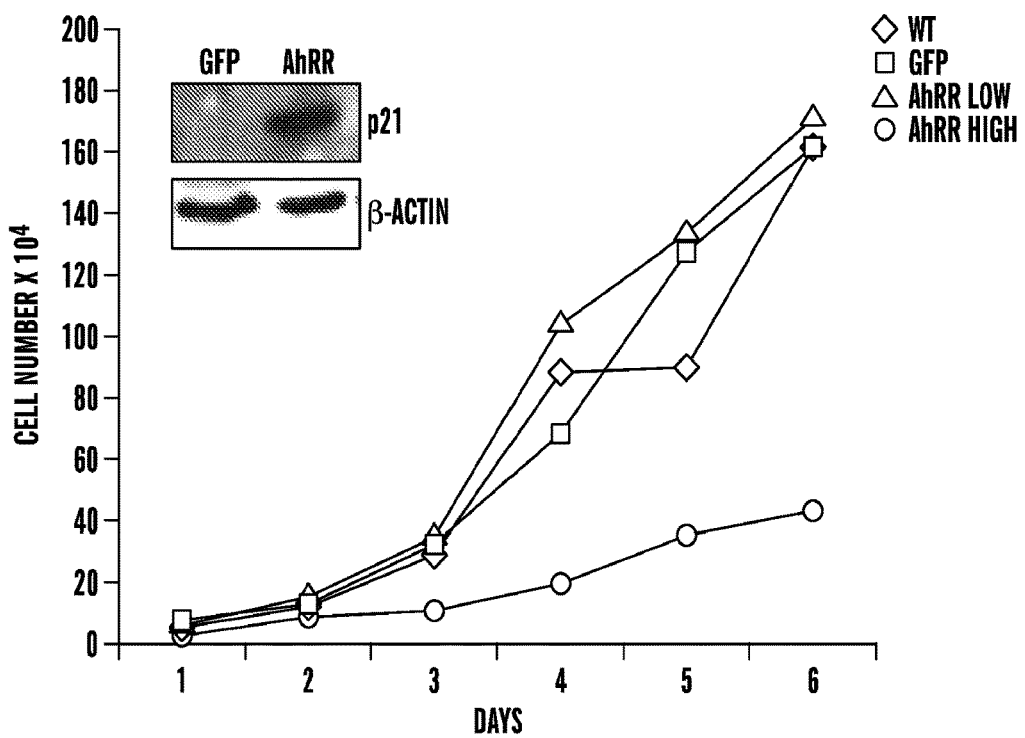
FIG. 1 shows that AhR inhibition with AhRR upregulates p21 and decreases MCF-10F growth. Insert: p21 protein levels in control or AhRR-transduced cells.

Described herein are novel compositions and methods comprising agents that modulate AhR activity. The inventors have discovered novel small molecule compounds of Formula (I) and (II), as described herein, that modulate constitutive AhR activity and can be used to treat and inhibit proliferative disorders such as cancer, based on the ability to inhibit cancer cell growth and other parameters that characterize tumor metastasis, such as tumor cell invasiveness.

Aryl Hydrocarbon Receptor and Modulators Thereof

The Aryl Hydrocarbon Receptor ("AhR") is a ligand-dependent member of the family of basic-helix-loop-helix transcription factors that has been found to be activated by numerous structurally diverse synthetic and naturally occurring compounds, such as polycyclic aromatic hydrocarbons, indoles, and flavonoids. In the absence of bound ligand, the AhR is present in a latent conformation in the cytoplasmic compartment of the cell associated with two molecules of the molecular chaperone heat shock protein 90 ("hsp90") (Perdew, J. Biol. Chem. 263:13802-13805 (1988) and Wilhelmsson et al., EMBO J. 9:69-76 (1990)), an immunophilin-like protein, XAP2 (Carver et al., J. Biol. Chem. 272: 11452-11456 (1997); Ma et al., J. Biol. Chem. 272:8878-8884 (1997); and Meyer et al., Mol. Cell. Biol. 18:978-988 (1998)), and the hsp90 interacting protein, p23 (Kazlauskas et al., J. Biol. Chem. 274:13519-13524 (1999)). Ligand binding initiates a cascade of events that includes translocation to the nucleus, release of hsp90, and heterodimerization with ARNT (Schmidt et al., Annu. Rev. Cell. Dev. Biol. 12:55-89 (1996) and Rowlands et al., Crit. Rev. Toxicol. 27:109-134 (1997)). The ligand bound AhR-ARNT complex is capable of recognizing consensus sequences termed dioxin-response elements ("DRE"s) located in the promoter region of CYP1A1 and other responsive genes, thereby activating transcription (Schmidt et al., Annu. Rev. Cell. Dev. Biol. 12:55-89 (1996) and Rowlands et al., Crit. Rev. Toxicol. 27:109-134 (1997)). Known examples of AhR-associated proteins include, but are not limited to, hsp90 p23, XAP2, p60, hsp70, and p48.

The AhR protein contains several domains critical for function and is classified as a member of the basic helix-loop-helix/Per-Arnt-Sim (bHLH/PAS) family of transcription factors. The bHLH motif is located in the N-terminal of the protein. Members of the bHLH superfamily have two functionally distinctive and highly conserved domains. The first is the basic-region (b) which is involved in the binding of the transcription factor to DNA. The second is the helix-loop-helix (HLH) region which facilitates protein-protein interactions. Also contained with the AhR are two PAS domains, PAS-A and PAS-B, which are stretches of 200-350 amino acids that exhibit a high sequence homology to the protein domains that were originally found in the Drosophila genes period (Per) and single minded (Sim) and in AhR's dimerization partner, the aryl hydrocarbon receptor nuclear translocator (ARNT). The PAS domains support specific secondary interactions with other PAS domain containing proteins, as is the case with AhR and ARNT, so that heterozygous and homozygous protein complexes can form. The ligand binding site of AhR is contained within the PAS-B domain and contains several conserved residues critical for ligand binding. Finally, a Q-rich domain is located in the C-terminal region of the protein and is involved in co-activator recruitment and transactivation.

Accordingly, the term "aryl hydrocarbon receptor" or "AhR" as used herein refers to the 848 amino acid polypeptide having the amino acid sequence of: MNSSSAN-ITYASRKRRKPVQKTVKPIPAEGIKSNPSKRHRDRLN-TELDRLASLLPFPQDVINKL DKLSVLRLSVSYLRAKSFFDVALKSSPTERNGGQDN-CRAANFREGLNLQEGEFLLQALNGFV LVVTTDALV-FYASSTIQDYLGFQQSDVIHQSVYELIHT-EDRAEFQRQLHWALNPSQCTESGQ GIEEATGLPQTVVCYNPDQIPPENSPLMERCFICRLR-CLLDNSSGFLAMNFQGKLKYLHGQKK KGKDGSILP-PQLALFAIATPLQPPSILEIRTKNFIFRTKHKLDFT-PIGCDAKGRIVLGYTEAELCT RGSGYQFIHAADMLYCAESHIRMIKTGESGMIV-FRLLTKNNRWTWVQSNARLLYKNGRPDY IIVTQR-PLTDEEGTEHLRKRNTKLPFMFTTGEAVLYEAT-NPFPAIMDPLPLRTKNGTSGKDSAT TSTLSKDSLNPSSLLAAMMQQDESIYLYPASSTS-STAPFENNFFNESMNECRNWQDNTAPMG NDTILKHEQIDQPQDVNSFAGGHPGLFQDSKNSDLY-SIMKNLGIDFEDIRHMQNEKFFRNDFS GEVD-FRDIDLTDEILTYVQDSLSKSPFIPSDYQQQQSLALNS-SCMVQEHLHLEQQQQHHQKQ VVVEPQQQLCQKMKHMQVNGMFENWNSNQFVPF-NCPQQDPQQYNVFTDLHGISQEFPYKS EMDSMPY-TQNFISCNQPVLPQHSKCTELDYPMGS-FEPSPYPTTSSLEDFVTCLQLPENQKHGL NPQSAIITPQTCYAGAVSMYQCQPEP-QHTHVGQMQYNPVLPGQQAFLNKFQNGVLNETYPA ELNNINNTQTTTHLQPLHHPSEARPFPDLTSSGFL (SEQ ID NO:1), as described by, e.g., NP_001612, together with any naturally occurring allelic, splice variants, and processed forms thereof. Typically, AhR refers to human AhR. The term AhR is also used to refer to truncated forms or fragments of the AhR polypeptide, comprising, for example, specific AhR domains. Reference to any such forms of the AhR can be identified in the application, e.g., by "AhR (122-224)."

During canonical signaling, cytosolic AhR binds to a ligand, such as a suitable small molecule, which facilitates AhR translocation to the nucleus and eventually results in de novo transcription of target genes. The promoters of AhR target genes have the responsive element 5'-TNGCGTG-3', termed "DRE" or "XRE" for "dioxin responsive elements" or "xenobiotic responsive elements." The genes for xenobiotic-metabolizing enzymes (e.g., cytochrome P450) are well-known targets of AhR and are referred to herein as "AhR battery genes." Hundreds of other genes also have DREs. Elucidation of the biochemistry of canonical AhR signaling has revealed several parameters that can fine-tune AhR activity. These include ligand characteristics, adapter molecules and transcriptional co-activators or co-repressors that regulate the extraordinary cell-specific activity of AhR (C. Esser et al., Trends in Immunology 2009, Vol. 30: 9, pp. 447-454).

Alternative pathways of AhR signaling have also been described. For instance, AhR can bind to retinoblastoma protein, estrogen receptor (ER), the transcription factor E2F1 and to the NFκB pathway subunits RelA and RelB. Evidence of AhR cross-talk with other signaling pathways, such as via kinases (src, JNK, p38, MAPK) or competition for transcription cofactors, has also been reported. AhR can act as a ubiquitin ligase, targeting the ER for proteasomal degradation. In these signaling pathways, AhR and the other proteins sometimes mutually repress each other's function. Indeed, bioinformatics analysis points to the existence of complex signal cross-talk between AhR and further transcription factors or transcription co-activators (C. Esser et al., Trends in Immunology 2009, Vol. 30: 9, pp. 447-454).

A number of low-molecular-weight chemicals qualify as endogenous or physiological "AhR ligands," that is, they have binding dissociation constants ($K_d$) and effective concentrations at the level expected for a physiologically relevant AhR ligand. Physical fluid shear stress (which causes oxidation of low-density lipoproteins), the second messengers cAMP and $Ca^{2+}$, serum and growth medium components all activate AhR responses (C. Esser et al., Trends in Immunology 2009, Vol. 30: 9, pp. 447-454). AhR has not yet been crystallized, so information on ligand-dependent structural changes is currently lacking. Ligand-protected protease digestion studies indicated that only one binding pocket for ligands exists (S. Kronenberg et al., Nucleic Acids Res. 28 (2000), pp. 2286-2291).

AhR ligands only need to meet minimal requirements for size and planar shape to fit into the AhR binding pocket. Consequently, a broad range of low-molecular-weight chemicals can activate AhR, albeit at different affinities ranging between $10^{-12}$ and $10^{-3}$ M. Many ligands have two carbon ring systems, such as tryptophan derivatives, flavonoids and biphenyls. The AhR system is genetically polymorphic and different alleles influence responsiveness to AhR ligands (C. Esser et al., Trends in Immunology 2009, Vol. 30: 9, pp. 447-454). AhR ligands can generally be classified into two categories, synthetic or naturally occurring. The first ligands to be discovered were synthetic and members of the halogenated aromatic hydrocarbons (dibenzo-dioxins, dibenzofurans and biphenyls) and polycyclic aromatic hydrocarbons (3-methylcholanthrene, benzo (a)pyrene, benzanthracenes and benzoflavones).

Naturally occurring compounds that have been identified as ligands of AhR include derivatives of tryptophan such as indigo and indirubin, tetrapyroles such as arachidonic acid metabolites lipoxin A4 and prostaglandin G, modified low-density lipoprotein and several dietary carotinoids.

Exemplary AhR ligands include, but are not limited to, endogenous ligands such as FICZ or 6-formylindolo[3,2-b] carbazole and 6,12-diformylindolo[3,2-b]carbazole or dFICZ (tryptophan photoproducts), bilirubin (product of heme metabolism by the liver), lipoxin A4 (eicosanoid with anti-inflammatory properties), ITE [2-(1' H-indole-3'-carbonyl)-thiazole-4-carboxylic acid methyl ester] (isolated from lung tissues); Environmental pollutants (formed during combustion of organic material) such as 2,3,7,8-tetrachlorodibenzo-p-dioxin (TCDD), and Benz[a]pyrene; dietary ligands, such as quercetin (present in apples and onions), indol-3-carbinol (present in many Brassicaceae, e.g. cabbage) resveratrol (present in red wine), and curcumin (a spice); and drugs (synthetic), such as M50367 {3-[2-(2-phenylethyl)

benzoimidazole-4-yl]-3-hydroxypropanoic acid, and VAF347 {[4-(3-chloro-phenyl)-pyrimidin-2-yll}.

Two of the most potent and well-characterized AhR antagonists include the synthetic flavonoid, 3'-methoxy-4' nitroflavone ("3M4NF"), and the indole derivative 3,3'-diindolylmethane ("DIM"). These compounds have been shown to function through direct competition for binding to the AhR ligand binding site (Henry et al., Mol. Pharmacol. 55:716-725 (1999); Hestermann et al., Mol. Cell. Biol 23:7920-7925 (2003)). The fate of the AhR upon binding of these structurally distinct antagonists is very different. Binding of 3M4NF to the AhR inhibits TCDD-mediated nuclear localization, ARNT dimerization, and DNA binding (Henry et al., Mol. Pharmacol. 55:716-725 (1999)). 3M4NF is believed to inhibit a conformational change within the AhR complex necessary for exposure of the nuclear localization sequence, resulting in retention of the AhR in the cytoplasmic compartment of the cell. Conversely, binding of DIM to the AhR allows nuclear localization, ARNT dimerization, and subsequent DNA binding. However, unlike the TCDD-bound AhR-ARNT dimer, this DIM-bound complex is incapable of recruiting the necessary co-factors responsible for initiating transcription (Hestermann et al., Mol. Cell. Biol 23:7920-7925 (2003)). Halogenated and nitro-substituted flavones can exhibit structure-dependent aryl hydrocarbon receptor (AhR) agonist and antagonist activities comparable to that observed for 2,3,7,8-tetrachlorodibenzo-p-dioxin (TCDD) (F. Lu et al., Biochemical Pharmacology. 51. 1077 (1996)).

AhR Modulators

The inventors have discovered that the novel flavone and hydroflavone AhR modulator compounds described herein, such as the small molecules of Formula (I) and Formula (II), e.g., CB7993113, CB9950998, and CMLD-2166, modulate constitutive AhR activity, by functioning as AhR inhibitors or non-constitutive AhR agonists. Further, they have discovered that such AhR modulator compounds can inhibit cancer cell growth, as well as tumor invasion, and are absorbed in vivo and can be used at pharmacologically effective doses to target peripheral organs, such as bone marrow. Accordingly, described herein are novel small molecule modulators of the AhR and constitutive AhR signaling for use in therapeutic compositions for, and methods of, treating and inhibiting cancer growth and tumor cell invasion, and other hyperproliferative disorders.

The AhR mediates a variety of functional responses, including, but not limited to de novo transcription of target genes or AhR battery genes having the DRE or XRE responsive element 5'-TNGCGTG-3'. Alternative pathways of AhR signaling have also been described, such as binding to retinoblastoma protein, estrogen receptor (ER), the transcription factor E2F1 and to the NFκB pathway subunits RelA and RelB. The AhR can also act as a ubiquitin ligase. Accordingly, signaling via the AhR comprises multiple pathways, including constitutive and non-constitutive AhR signaling pathways or signaling activity, as those terms are defined herein.

As used herein, "constitutive AhR signaling" refers to one or more signaling pathways mediated or regulated by the AhR that are activated or driven by one or more endogenous AhR ligands, or one or more environmental ligands, such as toxins or pollutants, that cause constitutive or long-term translocation of the AhR to the nucleus, and activation or modulation of one or more AhR battery genes involved in unregulated cell growth and proliferation, tumor cell invasiveness, or a combination thereof.

Accordingly, a "constitutive AhR agonist" is an AhR agonist that selectively binds to the AhR and can induce AhR activity or signaling or activate AhR function by itself, as measured or assayed using any method known to one of skill in the art, such as an in vitro AhR reporter assay, and can cause unregulated cell growth, tumor cell invasiveness, or a combination thereof. In some embodiments, a constitutive AhR agonist up-regulates expression of CYP1A1, CYP1B1, or a combination thereof. Activation by an AhR agonist is achieved when the activity value of the AhR is at least 10% greater, at least 25% greater, at least 50% greater, at least 75% greater, at least 100% greater, at least 2-fold greater, at least 5-fold greater, at least 10-fold greater, at least 25-fold greater, at least 50-fold greater, at least 100-fold greater, at least 1000-fold greater, or more, relative to a control in the absence of the AhR agonist.

As used herein, "non-constitutive AhR signaling" refers to one or more signaling pathways mediated or induced by the AhR that does not cause constitutive or long-term translocation of the AhR to the nucleus, nor activation or modulation of one or more AhR battery genes involved in unregulated cell growth, tumor cell invasiveness, or a combination thereof. In some embodiments, non-constitutive AhR signaling does not cause upregulation of expression of CYP1A1, CYP1B1, or a combination thereof.

Accordingly, an "AhR modulator," as the term is used herein refers to an agent, such as a small molecule of Formula (I), e.g., small molecules of formula (Ia), or Formula (II), e.g., small molecules of formula (IIa), that modulates or causes or facilitates a qualitative or quantitative change, alteration, or modification in one or more processes, mechanisms, effects, responses, functions, activities or pathways mediated by the AhR receptor. Such changes mediated by an AhR modulator, such as an inhibitor or a non-constitutive agonist of the AhR described herein, can refer to a decrease or an increase in the expression, activity or function of the AhR, such as a decrease in, inhibition of, or diversion of, constitutive activity of the AhR. The term "expression," refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "modulate" in reference to an Ahr modulator is used consistently with its use in the art, e.g., meaning to cause or facilitate a qualitative or quantitative change, alteration, or modification in one or more biological processes, mechanisms, effects, responses, functions, activities, pathways, or other phenomena of interest. Accordingly, as used herein, modulate refers to a qualitative or quantitative change, alteration, or modification in one or more processes, mechanisms, effects, responses, functions, activities or pathways mediated by the AhR receptor.

The term "agent" as used herein in reference to an AhR modulator means any compound or substance such as, but not limited to, a small molecule, nucleic acid, polypeptide, peptide, drug, ion, etc. An "agent" can be any chemical, entity, or moiety, including, without limitation, synthetic and naturally-occurring proteinaceous and non-proteinaceous entities. In some embodiments, an agent is a nucleic acid, a nucleic acid analogue, a protein, an antibody, a peptide, an aptamer, an oligomer of nucleic acids, an amino acid, or a carbohydrate, and includes, without limitation, proteins, oligonucleotides, ribozymes, DNAzymes, glycoproteins, siRNAs, lipoproteins, aptamers, and modifications and combinations thereof etc. In certain embodiments, as described herein, agents are small molecules having a chemical moiety. For example, chemical moieties include unsubstituted or substituted alkyl, aromatic, or heterocyclyl moieties. Compounds can be known to have a desired activity and/or property, e.g., modulate AhR activity, or can be selected from a library of diverse compounds, using, for example, the screening methods described herein.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In some embodiments, an AhR modulator selectively binds to the AhR. As used herein, "selectively binds" or "specifically binds" refers to the ability of an AhR agonist or AhR inhibitor, such as an AhR antagonist, described herein to bind to a target, such as the AhR polypeptide, with a $K_D$ $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. For example, if an agonist or inhibitor described herein binds to the AhR polypeptide with a $K_D$ of $10^{-5}$ M or lower, but not to other molecules, or a related homologue, then the agent is said to specifically bind the AhR polypeptide. Specific binding can be influenced by, for example, the affinity and avidity of the agonist or inhibitor and the concentration of the agonist or inhibitor used. The person of ordinary skill in the art can determine appropriate conditions under which the agonists or inhibitors described herein selectively bind using any suitable methods, such as titration of an AhR agonist or AhR inhibitor in a suitable cell binding assay, such as those described herein.

With respect to the AhR target, the term "ligand interaction site" on the AhR means a site, epitope, antigenic determinant, part, domain or stretch of amino acid residues on the AhR that is a site for binding to a ligand, receptor or other binding partner, a catalytic site, a cleavage site, a site for allosteric interaction, a site involved in multimerisation (such as homomerization or heterodimerization) of the AhR; or any other site, epitope, antigenic determinant, part, domain or stretch of amino acid residues on the AhR that is involved in a biological action or mechanism of the target, i.e., the AhR. More generally, a "ligand interaction site" can be any site, epitope, antigenic determinant, part, domain or stretch of amino acid residues on the AhR polypeptide to which an inhibitor or agonist described herein can bind, such that AhR activity and/or expression is (and/or any pathway, interaction, signalling, biological mechanism or biological effect in which the AhR is involved) is modulated.

In some aspects of the compositions and methods described herein, AhR modulators are AhR inhibitors having the chemical structures of Formula (I), Formula (Ia), Formula (II), or Formula (IIa) described herein.

As used herein, the terms "inhibitor of AhR" or "AhR inhibitor" refers to an agent or compound, such as the small molecules of Formula (I) or Formula (II) described herein, e.g., CB7993113 and CMLD-2166 respectively, that inhibits one or more AhR signaling and downstream effector pathways, including constitutive AhR signaling, as those terms are used herein. Thus, the term AhR inhibitor refers to an agent that inhibits expression of the AhR polypeptide or polynucleotide encoding the AhR, or one that binds to, partially or totally blocks stimulation, decreases, prevents, delays activation, inactivates, desensitizes, or down regulates the activity of the AhR polypeptide or polynucleotide encoding the AhR. Such AhR inhibitors can e.g., inhibit AhR expression, e.g., AhR translation, post-translational processing of the AhR, stability, degradation, or nuclear or cytoplasmic localization of the AhR polypeptide, or transcription, post transcriptional processing, stability or degradation of a polynucleotide encoding the AhR, or bind to, partially or totally block stimulation, DNA binding, or transcription factor activity of the AhR. An AhR inhibitor can act directly or indirectly. In some embodiments, an AhR inhibitor selectively binds to the AhR.

The terms "inhibit," "decrease," and "reduce", are all used herein generally to mean a decrease by a statistically significant amount. Accordingly, AhR inhibition is achieved when the activity value of an AhR polypeptide, or a polynucleotide encoding the AhR is about at least 10% less, at least 20% less, at least 30% less, at least 40% less, at least 50% less, at least 60% less, at least 70% less, at least 80% less, at least 90% less, at least 95% less, at least 98% less, at least 99% less, up to including 100% or less, i.e., absent, or undetectable, in comparison to a reference or control level in the absence of the inhibitor. In some embodiments of the aspects described herein, the AhR inhibitors inhibit constitutive AhR activity.

In some embodiments of these aspects, the AhR inhibitor is an "AhR antagonist." An AhR antagonist refers to an AhR inhibitor that does not provoke a biological response itself upon specifically binding to the AhR polypeptide or polynucleotide encoding the AhR, but blocks or dampens agonist-mediated or ligand-mediated responses, i.e., an AhR antagonist can bind but does not activate the AhR polypeptide or polynucleotide encoding the AhR, and the binding disrupts the interaction, displaces an AhR agonist, and/or inhibits the function of an AhR agonist. In some such embodiments, the AhR inhibitor is an AhR antagonist that prevents or inhibits binding of 2,3,7,8-tetrachlorodibenzo-p-dioxin (TCDD) to the AhR. In some such embodiments, an AhR antagonist is identified as a small molecule compound that blocks activation of the AhR by a strong AhR activator, such as BNF or TCDD, but does not induce AhR activity or signaling by itself, as measured or assayed using any method known to one of skill in the art, such as in vitro AhR reporter assays. Thus, as used herein, an AhR antagonist does not function as an inducer of AhR activity when bound to the AhR, i.e., they function as pure AhR inhibitors. In some embodiments, an AhR antagonist selectively binds to the AhR.

In some embodiments of these aspects, the AhR inhibitors described herein, such as the small molecules of Formula (I) or Formula (II), e.g., CB7993113 and CMLD-2166 respectively, block constitutive AhR effector functions that mediate growth and progression of established tumors. In other embodiments, the small molecule AhR inhibitors of Formula (I) or Formula (II), e.g., CB7993113 and CMLD-2166, described herein act as chemopreventatives by blocking AhR-mediated CYP1A1 induction and mutagen production on exposure to environmental ligands.

In some embodiments of these aspects, the small molecule AhR inhibitors of Formula (I) or Formula (II), e.g., CB7993113 and CMLD-2166, described herein inhibit the early contributions of constitutively active AhR in driving malignant transformation. In some embodiments, the small molecule AhR inhibitors of Formula (I) or Formula (II), e.g., CB7993113 and CMLD-2166, described herein inhibit constitutive AhR signaling-mediated cancer or tumor cell growth. In some embodiments, the small molecule AhR inhibitors of Formula (I) or Formula (II), e.g., CB7993113 and CMLD-2166, described herein inhibit constitutive AhR signaling-mediated tumor invasion in driving malignant transformation.

In other aspects, the AhR modulators described herein are non-constitutive AhR agonists having the chemical structures of Formula (I) or Formula (II), such as CB7950998.

As used herein, the terms "non-constitutive agonist of AhR, "non-constitutive AhR agonist", "non-constitutive activator of AhR," or "non-constitutive AhR activator" refer to a small molecule of Formula (I) or Formula (II) described herein, e.g., CB7950998, that binds to the AhR and hyperactivates or diverts constitutive AhR signaling and downstream effector pathways, as those terms are used herein. Such small molecule non-constitutive AhR agonists of Formula (I) or Formula (II), e.g., CB7950998, can increase expression of the AhR polypeptide or polynucleotide encoding the AhR, or bind to the AhR, and partially or totally divert constitutive AhR signaling and downstream activity, such as cancer cell growth and tumor invasive properties. In some embodiments, a non-constitutive AhR agonist selectively binds to the AhR.

In some embodiments of these aspects, the non-constitutive AhR agonist blocks or dampens constitutive endogenous ligand-mediated responses, i.e., a non-constitutive AhR agonist can bind and signal via the AhR, but does not activate the constitutive activity of the AhR polypeptide or polynucleotide encoding the AhR, and the binding disrupts the interaction and/or inhibits the function of an endogenous AhR ligand activating the constitutive AhR pathway. Accordingly, a non-constitutive AhR agonist of Formula (I) or Formula (II), e.g., CB7950998, can divert constitutive AhR signaling by about at least 10% or more, at least 20% or more, at least 30% or more, at least 40% or more, at least 50% or more, at least 60% or more, at least 70% or more, at least 80% or more, at least 90% or more, at least 95% or more, or at least 100% or completely in comparison to a reference or control level in the absence of the non-constitutive AhR agonist.

In preferred embodiments of these aspects, the non-constitutive AhR agonists of Formula (I) or Formula (II), e.g., CB7950998, described herein, bind the AhR and mediate non-constitutive AhR signaling, and inhibit or block constitutive AhR effector functions that mediate growth and progression of established tumors. In other embodiments, the non-constitutive AhR agonists of Formula (I) or Formula (II), e.g., CB7950998, described herein act as chemopreventatives by blocking AhR-mediated CYP1A1 induction and mutagen production on exposure to AhR ligands that mediate constitutive AhR signaling. In some embodiments, the non-constitutive AhR agonists of Formula (I) or Formula (II), e.g., CB7950998, described herein, inhibit the early contributions of constitutively active AhR in driving malignant transformation. In some embodiments, the non-constitutive AhR agonists of Formula (I) or Formula (II), e.g., CB7950998, described herein, inhibit or prevent cancer or tumor cell growth mediated by, in part or totally, constitutive AhR signaling. In some embodiments, the non-constitutive AhR agonists of Formula (I) or Formula (II), e.g., CB7950998, described herein, inhibit or prevent tumor invasiveness mediated by, in part or totally, constitutive AhR signaling.

In some embodiments, a non-constitutive AhR agonist is identified as a small molecule compound that: binds the AhR, and can displace binding by an AhR activator, such as BNF or TCDD; can activate the AhR, as measured or assayed using any method known to one of skill in the art; and does not cause, and preferably inhibits, cancer cell growth or proliferation or tumor invasiveness, as measured using any assay known to one of skill in the art. Activation of the AhR by a non-constitutive agonist can be measured using, for example, any of the in vitro AhR reporter assays described herein. Assays to determine whether an AhR agonist functions as a non-constitutive AhR agonist that inhibits cancer cell growth and proliferation can be based on any method known to one of skill in the art, such as the Matrigel assays described in the identification of CB7950998 at FIGS. 14A-14B.

Accordingly, provided for use in the various aspects described herein are small molecule AhR inhibitor and non-constitutive AhR agonist compounds of Formula (I):

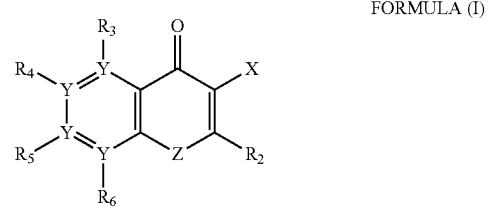

FORMULA (I)

wherein:
Y is C or N;
X is $OR_1$, $NHR_1$, $SR_1$, $CH_2(n)R_1$, halo, or H;
n is 0-6;
Z is O, S, or NH;
$R_1$, and $R_2$ are independently H, alkyl, alkenyl, alkynyl, amino, aminosulfonyl, alkoxy, acyl, aryl, heteroaryl, arylalkyl, cycloalkyl, heteroarylalkyl, heterocyclyl, or haloalkyl, each of which may be optionally substituted;
$R_3$, $R_4$, $R_5$ and $R_6$ are independently absent, H, halo, alkyl, alkenyl, alkynyl, alkoxy, acyl, aryl, heteroaryl, arylalkyl, cycloalkyl, heteroarylalkyl, heterocyclyl, or haloalkyl, each of which may be optionally substituted;
pharmaceutically acceptable salts thereof.

Also provided for use in the various aspects described herein are compounds of Formula (II):

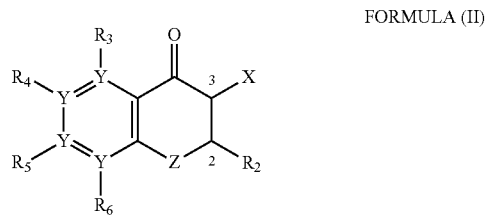

FORMULA (II)

wherein:
Y is C or N;
X is $OR_1$, $NHR_1$, $SR_1$, $CH_2(n)R_1$, halo, or H;
n is 0-6;
Z is O, S, or NH;

$R_1$, and $R_2$ are independently H, alkyl, alkenyl, alkynyl, amino, aminosulfonyl, alkoxy, acyl, aryl, heteroaryl, arylalkyl, cycloalkyl, heteroarylalkyl, heterocyclyl, or haloalkyl, each of which may be optionally substituted;

$R_3$, $R_4$, $R_5$ and $R_6$ are independently absent, H, halo, alkyl, alkenyl, alkynyl, alkoxy, acyl, aryl, heteroaryl, arylalkyl, cycloalkyl, heteroarylalkyl, heterocyclyl, or haloalkyl, each of which may be optionally substituted;

stereoisomers thereof; and pharmaceutically acceptable salts thereof.

As will be appreciated by one skilled in the art, various stereoisomers of Formula (II) can be prepared. For instance, stereoisomers focused on the two chiral centers (marked 2 and 3 in Formula (II)), represent (2R, 3S), (2S, 3R), (2R, 3R), and (2S, 3S) stereoisomers of the compound. Whether a chiral center is oriented in an R configuration or an S configuration will, of course, depend on the substituents accorded to the different variables. The following generic stereoisomers are examples of the various (2R, 3S), (2S, 3R), (2R, 3R), and (2S, 3S) configurations of Formula (II):

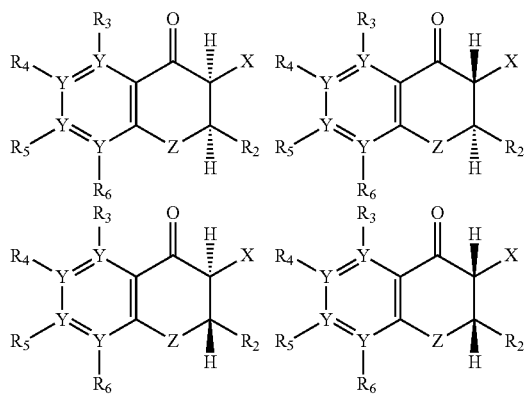

In some embodiments, Formula (I) can be represented as Formula (Ia):

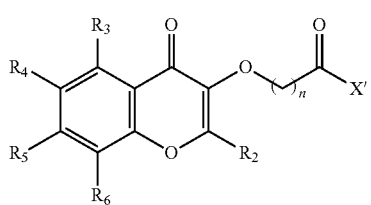

FORMULA (Ia)

wherein:

X' is H, alkyl, aminosulfonyl, alkoxy, amino, acyl, aryl, or heteroaryl, each of which may be optionally substituted;

n is 0-6;

$R_2$ is H, alkyl, acyl, aryl, heteroaryl, arylalkyl, cycloalkyl, heteroarylalkyl, heterocyclyl, or haloalkyl, each of which may be optionally substituted;

$R_3$, $R_4$, $R_5$ and $R_6$ are independently H, alkyl, acyl, halo, aryl, or heteroaryl, each of which may be optionally substituted; and pharmaceutically acceptable salts thereof.

In other embodiments of Formula (Ia), X' is alkyl, alkoxy, amino, aminosulfonyl (optionally substituted with aryl, or aralkyl groups such as toluene); n is 0 or 1; $R_2$ is aryl, substituted aryl, heteroaryl, or substituted aryl; and $R_3$, $R_4$, $R_5$ and $R_6$ are independently H, alkoxy, alkyl, or halo.

Representative compounds of Formula I include the following compounds:

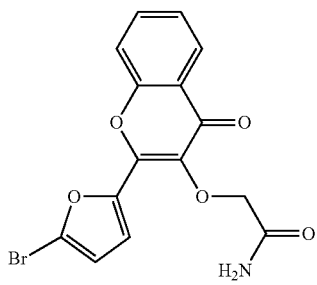 [SMILES: NC(=O)COc1c(-c2ccc(Br)o2)oc2ccccc2c1=O]

CB7993113

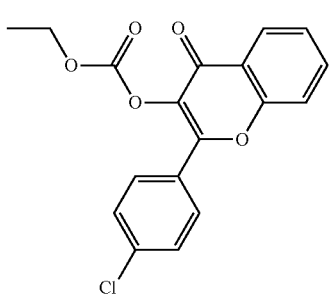

CB7950998

In other embodiments, Formula (II) can be represented as Formula (IIa):

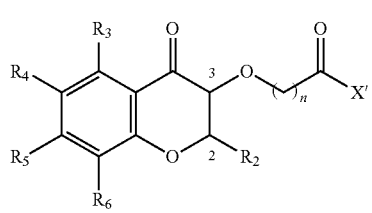

FORMULA (IIa)

wherein:

X' is H, alkyl, aminosulfonyl, alkoxy, acyl, aryl, or heteroaryl, each of which may be optionally substituted;

n is 0-6;

$R_2$ is H, alkyl, acyl, aryl, heteroaryl, arylalkyl, cycloalkyl, heteroarylalkyl, heterocyclyl, or haloalkyl, each of which may be optionally substituted;

$R_3$, $R_4$, $R_5$ and $R_6$ are independently H, alkyl, acyl, halo, aryl, or heteroaryl, each of which may be optionally substituted;

stereoisomers thereof; and pharmaceutically acceptable salts thereof.

In other embodiments of Formula (IIa), X' is alkyl, alkoxy, aminosulfonyl (optionally substituted with aryl, or aralkyl groups such as toluene); n is 0 or 1; $R_2$ is aryl, substituted aryl, heteroaryl, or substituted aryl; and $R_3$, $R_4$, $R_5$ and $R_6$ are independently H, alkoxy, alkyl, or halo.

Representative compounds of Formula II include the following compounds:

CMLD-2166

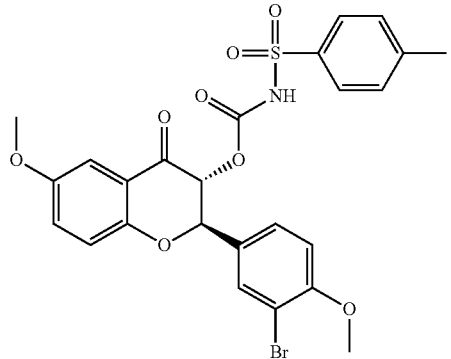

For simplicity, chemical moieties as defined and referred to throughout can be univalent chemical moieties (e.g., alkyl, aryl, etc.) or multivalent moieties under the appropriate structural circumstances clear to those skilled in the art. For example, in some embodiments, an "alkyl" moiety can refer to a monovalent radical (e.g. $CH_3$—$CH_2$—)$_9$ or in other embodiments, a bivalent linking moiety can be "alkyl," in which case those skilled in the art will understand the alkyl to be a divalent radical (e.g., —$CH_2$—$CH_2$—)$_9$ which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "halo" refers to any radical of fluorine, chlorine, bromine or iodine.

The term "acyl" refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions.

The term "alkyl" refers to saturated non-aromatic hydrocarbon chains that may be a straight chain or branched chain, containing the indicated number of carbon atoms (these include without limitation methyl, ethyl, propyl, butyl, pentyl, hexanyl, which may be optionally inserted with N, O, S, SS, $SO_2$, C(O), C(O)O, OC(O), C(O)N or NC(O). For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "alkoxy" refers to an —O-alkyl radical.

The term "aminoalkyl" refers to an alkyl substituted with an amino.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "arylalkyl" refers to alkyl substituted with an aryl or aryl substituted with an alkyl.

The term "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heteroarylalkyl" refers to an alkyl substituted with a heteroaryl.

The term "heterocyclyl" refers to a non-aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examplary heterocyclyl groups include, but are not limited to piperazinyl, pyrrolidinyl, dioxanyl, morpholinyl, tetrahydrofuranyl, and the like.

The term "haloalkyl" refers to an alkyl group having one, two, three or more halogen atoms attached thereto. Exemplary haloalkyl groups include, but are not limited to chloromethyl, bromoethyl, trifluoromethyl, and the like.

The term "optionally substituted" means that the specified group or moiety, such is unsubstituted or is substituted with one or more (typically 1-4 substituents) independently selected from the group of substituents listed herein in the definition for "substituents" or otherwise specified. The substituents may be "separate" substituents, for instance, a halo group and an alkoxy groups bonded to different carbon atoms in a benzene ring, or the substituents may be "stacked" on one another, for instance, an acyl group (such as formyl) that is substituted with an aminosulfonyl group that is substituted with an arylalkyl (such as toluene).

The term "substituents" refers to a group that replaces a hydrogen at any atom of the substituted group or moiety, as well as a group "substituted" on an alkyl, alkenyl, alkynyl, cycloalkyl, aryl, heterocyclyl, heteroaryl, acyl, amino group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, aminosulfonyl, acylamino, alkylcarbanoyl, arylcarbanoyl, aminoalkyl, alkoxycarbonyl, carboxy, hydroxyalkyl, alkylthio, $CF_3$, N-morphilino, phenylthio, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

In many cases, protecting groups are used during preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron* 1992, 48, 2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991. Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Nitrogen- or amino-protecting groups stable to acid treatment are selectively removed with base treatment, and are used to make reactive amino groups selectively available for substitution. Exemplary amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl.

AhR Modulators: Therapeutic Uses and Pharmaceutical Compositions

Described herein are novel small molecule AhR modulators of Formula (I) or Formula (II) for use in methods of treating a subject having or at risk for developing a proliferative disorder, such as a cancer. The small molecule AhR modulators of Formula (I) or Formula (II) described herein, such as AhR inhibitors e.g., CB7993113 and CMLD-2166, and non-constitutive AhR agonists, e.g., CB7950998, can be administered to a subject in need thereof by any appropriate route which results in an effective treatment in the subject.

Accordingly, in some aspects, provided herein are methods of modulating constitutive AhR activity in a subject. Such methods comprise administering to a subject having constitutive AhR activity a therapeutically effective amount of a small molecule AhR modulators of Formula (I) or Formula (II) described herein. In some embodiments of these aspects, the AhR modulator is an AhR inhibitor of Formula (I), e.g., CB7993113. In some embodiments of these aspects, the AhR modulator is an AhR inhibitor of Formula (II), e.g., CMLD-2166. In some embodiments of these aspects, the AhR modulator is a non-constitutive AhR agonist of Formula (I), e.g., CB7950998, or Formula (II).

The terms "subject" and "individual" are used interchangeably herein, and refer to an animal, for example a human, recipient of the small molecule AhR modulators of Formula (I) or Formula (II) described herein, e.g., AhR inhibitors, such as CB7993113 and CMLD-2166, and non-constitutive AhR agonists, such as CB7950998. For treatment of those disease states which are specific for a specific animal, such as a human subject, the term "subject" refers to that specific animal. The terms 'non-human animals' and 'non-human mammals' are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish.

In some aspects, provided herein are methods of treatment of a subject having a cancer or a cancerous condition, or at risk for cancer or a cancerous condition, the methods comprising administering to a subject having a cancer or cancerous condition, or at risk for cancer or a cancerous condition, a therapeutically effective amount of a small molecule AhR modulators of Formula (I) or Formula (II) described herein. In some embodiments of these aspects, the AhR modulator is an AhR inhibitor of Formula (I), e.g., CB7993113. In some embodiments of these aspects, the AhR modulator is an AhR inhibitor of Formula (II), e.g., CMLD-2166. In some embodiments of these aspects, the AhR modulator is a non-constitutive AhR agonist of Formula (I), e.g., CB7950998, or Formula (II).

The terms "cancer" and "cancerous" refer to or describe the physiological condition in mammals that is typically characterized by unregulated cell growth or proliferation, which interferes with the normal functioning of the bodily organs and systems. Accordingly, the terms "cancer" or "tumor" as used herein refers to an uncontrolled growth of cells which interferes with the normal functioning of the bodily organs and systems, including cancer stem cells and tumor vascular niches. A subject that has a cancer or a tumor is a subject having objectively measurable cancer cells present in the subject's body. Cancers which migrate from their original location and seed vital organs can eventually lead to the death of the subject through the functional deterioration of the affected organs. Hematopoietic cancers, such as leukemia, are able to out-compete the normal hematopoietic compartments in a subject, thereby leading to hematopoietic failure (in the form of anemia, thrombocytopenia and neutropenia) ultimately causing death. Included in this definition are benign and malignant cancers, as well as dormant tumors or micrometastatses.

A "metastasis" refers to the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Accordingly, cancers that can be treated using the compositions and methods described in the various aspects herein include, but are not limited to, carcinoma, lymphoma, blastoma, sarcoma, and leukemia. More particular examples of such cancers include, but are not limited to, breast cancer; basal cell carcinoma, biliary tract cancer; bladder cancer; bone cancer; brain and CNS cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; glioblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, a cancer can be a solid tumor. As used herein, a "solid tumor" refers to an abnormal mass of tissue that usually does not contain cysts or liquid areas. Solid tumors can be benign or malignant. Different types of solid tumors are named for the type of cells that form them. Non-limiting examples of solid tumors are sarcomas, carcinomas, and lymphomas. Leukemias and other cancers of the blood generally do not form solid tumors and are not hence encompassed by the term 'solid tumor' as used herein.

In some embodiments of the aspects described herein, a subject refers to a human subject having a cancer or at increased risk for a cancerous condition. A subject that has a cancer or a tumor is a subject having objectively measurable cancer cells present in the subject's body. A subject that has increased risk for a cancerous condition includes subjects with a known genetic risk factor for cancer, or for whom there is a familial history of cancer. In some such embodiments of the aspects described herein, the cancer is a breast cancer. In some such embodiments of the aspects described herein, the cancer is a solid tumor.

In some embodiments of the aspects described herein, the methods of treating cancer or a cancerous condition further comprise the step of selecting, diagnosing, or identifying a subject having cancer or a cancerous condition. In such embodiments, a subject is identified as having cancer by objective determination of the presence of cancer cells or a tumor in the subject's body by one of skill in the art. Such objective determinations can be performed through the sole or combined use of tissue biopsies, blood and platelet cell counts, urine analyses, magnetic resonance imaging (MRI) scans, computed tomography (CT) scans, liver function studies, chest X-rays and bone scans in addition to the monitoring of specific symptoms associated with a cancer.

Administration, Dosages, and Durations

A small molecule AhR modulator of Formula (I) or Formula (II) described herein, e.g., AhR inhibitors, such as CB7993113 and CMLD-2166, and non-constitutive AhR agonists, such as CB7950996, can be formulated, dosed, and administered in a fashion consistent with good medical practice for use in the treatment of the cancers and cancerous conditions described herein, such as breast cancer. Factors for consideration in this context include the particular disorder or type of disorder, e.g., cancer, being treated, the particular subject being treated, the clinical condition of the individual subject, the cause of the disorder, the site of delivery of the agent, the method of administration, the scheduling of administration, and other factors known to medical practitioners.

Accordingly, the "therapeutically effective amount" of a small molecule AhR modulator of Formula (I) or Formula (II) described herein, e.g., AhR inhibitors, such as CB7993113 and CMLD-2166, and non-constitutive AhR agonists, such as CB7950996, to be administered is governed by such considerations, and, as used herein, refers to the minimum amount necessary to prevent, ameliorate, or treat, or stabilize, a disorder or condition, such as one mediated by constitutive AhR activity.

In those aspects and embodiments relating to cancer or other proliferative disorders, the therapeutically effective amount of a small molecule AhR modulator of Formula (I) or Formula (II) described herein is the minimum amount necessary to, for example, increase the time until progression (duration of progression free survival), to inhibit or prevent tumor invasion, or to treat or prevent the occurrence or recurrence of a tumor, a dormant tumor, or a micrometastases. In some such embodiments, a small molecule AhR modulator of Formula (I) or Formula (II) described herein, e.g., an AhR inhibitor, such as CB7993113 and CMLD-2166, or a non-constitutive AhR agonist, such as CB7950996, is optionally formulated with one or more agents currently used to prevent or treat cancer or a risk of developing a cancer. The effective amount of such other agents depends on the amount of AhR inhibitor or non-constitutive AhR agonist present in the formulation, the type of disorder or treatment, and other factors discussed herein, and as understood by one of skill in the art. These are generally used in the same dosages and with administration routes as used herein before or about from 1 to 99% of the heretofore employed dosages.

An effective amount as used herein also includes an amount sufficient to delay the development of a symptom of the cancer, alter the course of a cancer (for example but not limited to, slow the progression of a symptom of the cancer, such as growth of a tumor), or reverse a symptom of the cancer or tumor. Thus, it is not possible to specify the exact "effective amount". However, for any given case, an appropriate "effective amount" can be determined by one of ordinary skill in the art using only routine experimentation.

Effective amounts, toxicity, and therapeutic efficacy of the small molecule AhR modulators of Formula (I) or Formula (II) described herein, e.g., an AhR inhibitor, such as CB7993113 and CMLD-2166, or a non-constitutive AhR agonist, such as CB7950996, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of the AhR inhibitor or non-constitutive AhR agonist), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Depending on the type and severity of the disease, about 1 µg/kg to 100 mg/kg (e.g., 0.1-20 mg/kg) of a small molecule AhR modulator of Formula (I) or Formula (II) described herein, e.g., an AhR inhibitor, such as CB7993113 and CMLD-2166, or a non-constitutive AhR agonist, such as CB7950996, is an initial candidate dosage range for administration to the subject, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until the cancer is treated, as measured by the methods described above or known in the art. However, other dosage regimens may be useful. The progress of the therapeutic methods described herein is easily monitored by conventional techniques and assays, such as those described herein, or known to one of skill in the art. In other embodiments, such dosing regimen is used in combination with a chemotherapy regimen as the first line therapy for treating locally recurrent or metastatic breast cancer.

The duration of the therapeutic methods described herein can continue for as long as medically indicated or until a desired therapeutic effect (e.g., those described herein) is achieved. In certain embodiments, administration of an AhR modulator, i.e., "AhR inhibitor therapy" or "non-constitutive AhR agonist therapy" is continued for at least 1 month, at least 2 months, at least 4 months, at least 6 months, at least 8 months, at least 10 months, at least 1 year, at least 2 years, at least 3 years, at least 4 years, at least 5 years, at least 10 years, at least 20 years, or for at least a period of years up to the lifetime of the subject.

The small molecule AhR modulators of Formula (I) or Formula (II) described herein, e.g., an AhR inhibitor, such as CB7993113 and CMLD-2166, or a non-constitutive AhR agonist, such as CB7950996, can be administered to a subject, e.g., a human subject, in accordance with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration can be used if, for example, extensive side effects or toxicity is associated with the AhR inhibitor or the non-constitutive AhR agonist. An ex vivo strategy can also be used for therapeutic applications.

Exemplary modes of administration of the small molecule AhR modulators of Formula (I) or Formula (II) described herein, e.g., an AhR inhibitor, such as CB7993113 and CMLD-2166, or a non-constitutive AhR agonist, such as CB7950996, include, but are not limited to, injection, infusion, inhalation (e.g., intranasal or intratracheal), ingestion, rectal, and topical (including buccal and sublingual) administration. The phrases "parenteral administration" and "administered parenterally" as used herein, refer to modes of administration other than enteral and topical administration, usually by injection. As used herein, "injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein refer to the administration of a small molecule AhR modulator of Formula (I) or Formula (II) described herein, e.g., an AhR inhibitor, such as CB7993113 and CMLD-2166, or a non-constitutive AhR agonist, such as CB7950996, other than directly into a target site, tissue, or organ, such as the lung, such that it enters the subject's circulatory system and, thus, is subject to metabolism and other like processes.

In some embodiments, the small molecule AhR modulators of Formula (I) or Formula (II) described herein, e.g., an AhR inhibitor, such as CB7993113 and CMLD-2166, or a non-constitutive AhR agonist, such as CB7950996, are administered by intravenous infusion or injection. In some embodiments, where local treatment is desired, for example, at or near a site of a tumor, such as a tumor in the breast in a subject having breast cancer, the small molecule AhR modulators of Formula (I) or Formula (II) described herein, e.g., an AhR inhibitor, such as CB7993113 and CMLD-2166, or a non-constitutive AhR agonist, such as CB7950996, can be administered by intralesional administration. Additionally, in some embodiments, the AhR inhibitor or non-constitutive AhR agonists described herein can be administered by pulse infusion, particularly with declining doses of the inhibitors or non-constitutive agonists. Preferably the dosing is given by injections, most preferably intravenous or subcutaneous injections, depending in part on whether the administration is brief or chronic.

In some embodiments, the small molecule AhR modulators of Formula (I) or Formula (II) described herein, e.g., an AhR inhibitor, such as CB7993113 and CMLD-2166, or a non-constitutive AhR agonist, such as CB7950996, is administered locally, e.g., by direct injections, when the disorder or location of the tumor permits, and the injections can be repeated periodically. The AhR inhibitors or non-constitutive AhR agonists described herein can also be delivered systemically to the subject or directly to the tumor cells, e.g., to a tumor or a tumor bed, following surgical excision of the tumor, in order to prevent or reduce local recurrence or metastasis, for example of a dormant tumor or micrometastases.

Pharmaceutical Formulations

Therapeutic formulations of AhR inhibitors can be prepared, in some aspects, by mixing a small molecule AhR modulator of Formula (I) or Formula (II) described herein, e.g., an AhR inhibitor, such as CB7993113 and CMLD-2166, or a non-constitutive AhR agonist, such as CB7950996, having the desired degree of purity with one or more pharmaceutically acceptable carriers, excipients or stabilizers (Remington's Pharmaceutical Sciences 16th edition, Osol, A. Ed. (1980)), in the form of lyophilized formulations or aqueous solutions. Such therapeutic formulations of the AhR inhibitors or non-constitutive AhR agonists described herein include formulation into pharmaceutical compositions or pharmaceutical formulations for parenteral administration, e.g., intravenous; mucosal, e.g., intranasal; enteral, e.g., oral; topical, e.g., transdermal; ocular, or other mode of administration.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the activity of, carrying, or transporting the small molecule AhR modulators of Formula (I) or Formula (II) described herein, e.g., an AhR inhibitor, such as CB7993113 and CMLD-2166, or a non-constitutive AhR agonist, such as CB7950996, from one organ, or portion of the body, to another organ, or portion of the body.

Some non-limiting examples of acceptable carriers, excipients, or stabilizers that are nontoxic to recipients at the dosages and concentrations employed, include pH buffered solutions such as phosphate, citrate, and other organic acids; antioxidants, including ascorbic acid and methionine; lubricating agents, such as magnesium stearate, sodium lauryl sulfate and talc; excipients, such as cocoa butter and suppository waxes; oils, such as peanut oil, cottonseed oil, safflower oil, sesame oil, olive oil, corn oil and soybean oil; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, HDL, LDL, or immunoglobulins; hydrophilic polymers, such as polyvinylpyrrolidone; amino acids such as glycine, glutamine, asparagine, histidine, arginine, or lysine; monosaccharides, disaccharides, and other carbohydrates including mannose, starches (corn starch or potato starch), or dextrins; cellulose, and its derivatives, such as sodium carboxymethyl cellulose, methylcellulose, ethyl cellulose, microcrystalline cellulose and cellulose acetate; chelating agents such as EDTA; sugars such as sucrose, glucose, lactose, mannitol, trehalose or sorbitol; salt-forming counter-ions such as sodium; metal complexes (e.g. Zn-protein complexes); glycols; such as propylene glycol; polyols, such as glycerin; esters, such as ethyl oleate and ethyl laurate; agar; buffering agents, such as magnesium hydroxide and aluminum hydroxide; alginic acid; pyrogen-free water; isotonic saline; Ringer's solution; polyesters, polycarbonates and/or polyanhydrides; $C_2$-$C_{12}$ alcohols, such as ethanol; powdered tragacanth; malt; and/or non-ionic surfactants such as TWEEN™, PLURONICS™ or polyethylene glycol (PEG); and/or other non-toxic compatible substances employed in pharmaceutical formulations. Wetting agents, coloring agents, release agents, coating agents, sweetening agents, flavoring agents, perfuming agents, preservative and antioxidants can also be present in the formulation.

In some embodiments, the therapeutic formulation comprising an AhR inhibitor comprises a pharmaceutically acceptable salt, typically, e.g., sodium chloride, and preferably at about physiological concentrations. Optionally, the formulations described herein can contain a pharmaceutically acceptable preservative. In some embodiments, the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

In some embodiments of the aspects described herein, a small molecule AhR modulator of Formula (I) or Formula (II) described herein, e.g., an AhR inhibitor, such as CB7993113 and CMLD-2166, or a non-constitutive AhR agonist, such as CB7950996, can be specially formulated for administration of the compound to a subject in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, a small molecule AhR modulator of Formula (I) or Formula (II) described herein, e.g., an AhR inhibitor, such as CB7993113 and CMLD-2166, or a non-constitutive AhR agonist, such as CB7950996, can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

In some embodiments, parenteral dosage forms of the small molecule AhR modulators of Formula (I) or Formula (II) described herein, e.g., an AhR inhibitor, such as CB7993113 and CMLD-2166, or a non-constitutive AhR agonist, such as CB7950996, can be administered to a subject with a cancer or at increased risk for cancer by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments, the small molecule AhR modulators of Formula (I) or Formula (II) described herein, e.g., an AhR inhibitor, such as CB7993113 and CMLD-2166, or a non-constitutive AhR agonist, such as CB7950996, are formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

Typical oral dosage forms of the compositions are prepared by combining the pharmaceutically acceptable salt of a small molecule AhR modulator of Formula (I) or Formula (II) described herein, e.g., an AhR inhibitor, such as CB7993113 and CMLD-2166, or a non-constitutive AhR agonist, such as CB7950996, in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Binders suitable for use in the pharmaceutical formulations described herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical formulations described herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions described herein is typically present in from about 50 to about 99 weight percent of the pharmaceutical composition.

Disintegrants are used in the oral pharmaceutical formulations described herein to provide tablets that disintegrate when exposed to an aqueous environment. A sufficient amount of disintegrant that is neither too little nor too much to detrimentally alter the release of the active ingredient(s) should be used to form solid oral dosage forms of the small molecule AhR modulators of Formula (I) or Formula (II) described herein, e.g., an AhR inhibitor, such as CB7993113 and CMLD-2166, or a non-constitutive AhR agonist, such as CB7950996. The amount of disintegrant used varies based upon the type of formulation, and is readily discernible to those of ordinary skill in the art. Disintegrants that can be used to form oral pharmaceutical formulations include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form oral pharmaceutical formulations of the AhR inhibitors described herein, include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In other embodiments, lactose-free pharmaceutical formulations and dosage forms are provided, wherein such compositions preferably contain little, if any, lactose or other mono- or di-saccharides. As used herein, the term "lactose-free" means that the amount of lactose present, if any, is insufficient to substantially increase the degradation rate of an active ingredient. Lactose-free compositions of the disclosure can comprise excipients which are well known in the art and are listed in the USP (XXI)/NF (XVI), which is incorporated herein by reference.

The oral formulations of the small molecule AhR modulators of Formula (I) or Formula (II) described herein, e.g., an AhR inhibitor, such as CB7993113 and CMLD-2166, or a non-constitutive AhR agonist, such as CB7950996, further encompass, in some embodiments, anhydrous pharmaceutical compositions and dosage forms comprising the AhR inhibitors or non-constitutive AhR agonists described herein as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

An AhR inhibitor described herein, such as a small molecule of Formula (I) or Formula (II), e.g., CB7993113 and CMLD-2166, can be administered directly to the airways in the form of an aerosol or by nebulization. Accordingly, for use as aerosols, in some embodiments, an AhR inhibitor described herein, such as a small molecule of Formula (I) or Formula (II), e.g., CB7993113 and CMLD-2166, may be packaged in a pressurized aerosol container together with suitable propellants, for example, hydrocarbon propellants like propane, butane, or isobutane with conventional adjuvants. In other embodiments, the AhR inhibitor can be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means, including by using many nebulizers known and marketed today. As is well known, any suitable gas can be used to apply pressure during the nebulization, with preferred gases being those which are chemically inert to the small molecule AhR modulators of Formula (I) or Formula (II) described herein, e.g., an AhR inhibitor, such as CB7993113 and CMLD-2166, or a non-constitutive AhR agonist, such as CB7950996. Exemplary gases include, but are not limited to, nitrogen, argon or helium.

In other embodiments, a small molecule AhR modulator of Formula (I) or Formula (II) described herein, e.g., an AhR inhibitor, such as CB7993113 and CMLD-2166, or a non-constitutive AhR agonist, such as CB7950996, can be administered directly to the airways in the form of a dry powder. For use as a dry powder, an AhR inhibitor or non-constitutive AhR agonist can be administered by use of an inhaler. Exemplary inhalers include metered dose inhalers and dry powdered inhalers.

Suitable powder compositions include, by way of illustration, powdered preparations of a small molecule AhR modulator of Formula (I) or Formula (II) described herein, e.g., an AhR inhibitor, such as CB7993113 and CMLD-2166, or a non-constitutive AhR agonist, such as CB7950996, thoroughly intermixed with lactose, or other inert powders acceptable for, e.g., intrabronchial administration. The powder compositions can be administered via an aerosol dispenser or encased in a breakable capsule which may be inserted by the subject into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S, and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

Topical dosage forms of the small molecule AhR modulators of Formula (I) or Formula (II) described herein, e.g., an AhR inhibitor, such as CB7993113 and CMLD-2166, or a non-constitutive AhR agonist, such as CB7950996, are also provided in some embodiments, and include, but are not limited to, creams, lotions, ointments, gels, shampoos, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure.

Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990). and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer a small molecule AhR modulator of Formula (I) or Formula (II) described herein, e.g., an AhR inhibitor, such as CB7993113 and CMLD-2166, or a non-constitutive AhR agonist, such as CB7950996, include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms of the inhibitors described herein are well known to those skilled in the pharmaceutical arts, and depend on the particular tissue or organ to which a given pharmaceutical composition or dosage form will be applied. In addition, depending on the specific tissue to be treated, additional components may be used prior to, in conjunction with, or subsequent to treatment with a small molecule AhR modulator of Formula (I) or Formula (II) described herein, e.g., an AhR inhibitor, such as CB7993113 and CMLD-2166, or a non-constitutive AhR agonist, such as CB7950996. For example, penetration enhancers can be used to assist in delivering the active ingredients to or across the tissue.

In some embodiments of the aspects described herein, the pharmaceutical formulations comprising the small molecule AhR modulators of Formula (I) or Formula (II) described herein, e.g., an AhR inhibitor, such as CB7993113 and CMLD-2166, or a non-constitutive AhR agonist, such as CB7950996, can further comprise more than one active compound as necessary for the particular indication being treated, preferably those with complementary activities that do not adversely affect each other. For example, in some embodiments, it can be desirable to further provide antibodies which bind to EGFR, VEGF, VEGFR, or ErbB2 (e.g., Herceptin™) in the formulation comprising the AhR inhibitor or non-constitutive AhR agonist of Formula (I) or Formula (II). In other embodiments, the formulation comprising the AhR inhibitor or non-constitutive AhR agonist of Formula (I) or Formula (II) can comprise a cytotoxic agent, cytokine, growth inhibitory agent and/or VEGFR antagonist. Such molecules are suitably present in combination in amounts that are effective for the purpose intended.

In some embodiments, the active ingredients of the formulations comprising AhR inhibitors and non-constitutive AhR agonists described herein, such as can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments of these aspects, the small molecule AhR modulators of Formula (I) or Formula (II) described herein, e.g., an AhR inhibitor, such as CB7993113 and CMLD-2166, or a non-constitutive AhR agonist, such as CB7950996, can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Chemg-ju, Controlled Release Dosage Form Design, 2 (Technomic Publishing, Lancaster, Pa.: 2000)). Controlled-release formulations can be used to control an AhR inhibitor's onset of action, duration of action, plasma levels within the therapeutic window, and peak blood levels. In particular, controlled- or extended-release dosage forms or formulations can be used to ensure that the maximum effectiveness of the small molecule AhR modulators of Formula (I) or Formula (II) described herein, e.g., an AhR inhibitor, such as CB7993113 and CMLD-2166, or a non-constitutive AhR agonist, such as CB7950996, is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the small molecule AhR modulators of Formula (I) or Formula (II) described herein, e.g., an AhR inhibitor, such as CB7993113 and CMLD-2166, or a non-constitutive AhR agonist, such as CB7950996. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated ins entirety herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

In some embodiments of the aspects, the small molecule AhR modulators of Formula (I) or Formula (II) described herein, e.g., an AhR inhibitor, such as CB7993113 and CMLD-2166, or a non-constitutive AhR agonist, such as CB7950996, for use in the various therapeutic formulations and compositions, and methods thereof, described herein, is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred in chronic conditions, such as cancer, as each pulse dose can be reduced and the total amount of a compound of an AhR inhibitor administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals may be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In some embodiments, sustained-release preparations comprising the small molecule AhR modulators of Formula (I) or Formula (II) described herein, e.g., an AhR inhibitor, such as CB7993113 and CMLD-2166, or a non-constitutive AhR agonist, such as CB7950996, can be prepared. Suitable examples of sustained-release preparations include semipermeable matrices of solid hydrophobic polymers containing the inhibitor, in which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations comprising the small molecule AhR modulators of Formula (I) or Formula (II) described herein, e.g., an AhR inhibitor, such as CB7993113 and CMLD-2166, or a non-constitutive AhR agonist, such as CB7950996, to be used for in vivo administration are preferably sterile. This is readily accomplished by filtration through, for example, sterile filtration membranes, and other methods known to one of skill in the art.

Efficacy of the Treatment

One key advantage of the methods, uses and compositions comprising the small molecule AhR modulators of Formula (I) or Formula (II) described herein, e.g., an AhR inhibitor, such as CB7993113 and CMLD-2166, or a non-constitutive AhR agonist, such as CB7950996, is the ability of producing marked anti-cancer effects in a human subject without causing significant toxicities or adverse effects. The efficacy of the treatments described herein can be measured by various parameters commonly used in evaluating cancer treatments, including but not limited to, tumor regression, tumor weight or size shrinkage, reduction in rate of tumor growth, the presence or the size of a dormant tumor, the presence or size of metastases or micrometastases, degree of tumor or cancer invasiveness, size or number of the blood vessels, time to progression, duration of survival, progression free survival, overall response rate, duration of response, and quality of life. For example, tumor shrinkage of greater than 50% in a 2-dimensional analysis is the standard cut-off for declaring a response. However, in some embodiments, the compositions comprising the small molecule AhR modulators of Formula (I) or Formula (II) described herein can be used to cause inhibition of metastatic spread without shrinkage of the primary tumor, or can simply exert a tumoristatic effect. In the case of cancers, the therapeutically effective amount of the compositions comprising the small molecule AhR modulators of Formula (I) or Formula (II) described herein can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the compositions comprising the small molecule AhR modulators of Formula (I) or Formula (II) described herein can prevent growth and/or kill existing cancer cells, it can be cytostatic and/or cytotoxic. For cancer therapy, efficacy in vivo can, for example, be measured by assessing the duration of survival, duration of progression free survival (PFS), the response rates (RR), duration of response, and/or quality of life.

In some embodiments, methods for increasing progression free survival of a human subject susceptible to or diagnosed with a cancer are described herein. "Time to disease progression," as used herein, is defined as the time from administration of the drug until disease progression or death. In a preferred embodiments, the method of treatments described herein using small molecule AhR modulators of Formula (I) or Formula (II) described herein, e.g., an AhR inhibitor, such as CB7993113 and CMLD-2166, or a non-constitutive AhR agonist, such as CB7950996, and, in some further embodiments, one or more chemotherapeutic agents, significantly increases progression free survival by at least about 1 month, at least about 2 months, at least about 3 months, at least about 4 months, at least about 5 months, at least about 6 months, at least about 7 months, at least about 8 months, at least about 9 months, at least about 10 months, at least about 11 months, when compared to no treatment or a treatment with chemotherapy alone.

In other embodiments, the methods of treatment described herein significantly increase response rate in a group of human subjects susceptible to or diagnosed with a cancer who are treated with various therapeutics. "Response rate," as used herein, is defined as the percentage of treated subjects who responded to the treatment. In some such embodiments, the combination treatments described herein comprising using a small molecule AhR modulator of Formula (I) or Formula (II), e.g., an AhR inhibitor, such as CB7993113 and CMLD-2166, or a non-constitutive AhR agonist, such as CB7950996, and, in some further embodiments, one or more chemotherapeutic agents, significantly increases response rate in the treated subject group compared to an untreated group or a group treated with chemotherapy alone.

In other embodiments of these methods, the administration of a small molecule AhR modulator of Formula (I) or Formula (II) described herein, e.g., an AhR inhibitor, such as CB7993113 and CMLD-2166, or a non-constitutive AhR agonist, such as CB7950996, is used for increasing duration of response in a human subject or a group of human subjects susceptible to or diagnosed with a cancer. As used herein, "duration of response" is defined as the time from the initial response to disease progression. In some such embodiments, the AhR inhibitors and non-constitutive AhR agonists described herein can be used for increasing the duration of survival of a human subject susceptible to or diagnosed with a cancer.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic immune condition, such as, but not limited to, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the small molecule AhR modulators of Formula (I) or Formula (II) described herein, e.g., an AhR inhibitor, such as CB7993113 and CMLD-2166, or a non-constitutive AhR agonist, such as CB7950996, described herein to a subject in order to alleviate a symptom of a cancer, or other such disorder. As used herein, "alleviating a symptom of a cancer" is ameliorating or reducing any condition or symptom associated with the cancer. As compared with an equivalent untreated control, such reduction or degree of prevention is at least 5%, 10%, 20%, 40%, 50%, 60%, 80%, 90%, 95%, or 100% as measured by any standard technique. Ideally, the cancer is completely cleared as detected by any standard method known in the art, in which case the cancer is considered to have been treated. A patient who is being treated for a cancer is one who a medical practitioner has diagnosed as having such a condition. Diagnosis can be by any suitable means. Diagnosis and monitoring can involve, for example, detecting the level of cancer cells in a biological sample (for example, a tissue or lymph node biopsy, blood test, or urine test), detecting the level of a surrogate marker of the cancer in a biological sample, detecting symptoms associated with the specific cancer, or detecting immune cells involved in the immune response typical of such a cancer infections.

Combination Therapies

In some embodiments, the compositions and methods comprising the novel the small molecule AhR modulators of Formula (I) or Formula (II) described herein, e.g., an AhR inhibitor, such as CB7993113 and CMLD-2166, or a non-constitutive AhR agonist, such as CB7950996, further comprise administration or treatment with one or more additional cancer therapies. Examples of anti-cancer therapies include, without limitation, surgery, radiation therapy (radiotherapy), biotherapy, immunotherapy, chemotherapy, or a combination of these therapies. In addition, cytotoxic agents, anti-angiogenic and anti-proliferative agents can be used in combination with the AhR inhibitor(s).

For the treatment of cancer in such embodiments comprising combination therapies, the appropriate dosage of a small molecule AhR modulator of Formula (I) or Formula (II) described herein, e.g., an AhR inhibitor, such as CB7993113 and CMLD-2166, or a non-constitutive AhR agonist, such as CB7950996, will depend on the type of disease to be treated, as defined above, the severity and course of the disease, whether the AhR inhibitor or non-constitutive AhR agonist is administered for preventive or therapeutic purposes, previous therapy, the subject's clinical history and response to the AhR inhibitor or non-constitutive AhR agonist, and the discretion of the attending physician. The AhR inhibitor or non-constitutive AhR agonist is suitably administered to the subject at one time or over a series of treatments.

In those embodiments where a combination therapy regimen is applied, a small molecule AhR modulator of Formula (I) or Formula (II) described herein, e.g., an AhR inhibitor, such as CB7993113 and CMLD-2166, or a non-constitutive AhR agonist, such as CB7950996, and one or more anti-cancer therapeutic agents as described herein are administered in a therapeutically effective or synergistic amount. As used in such embodiments encompassing combination therapies, a therapeutically effective amount is such that co-administration of a small molecule AhR modulator of Formula (I) or Formula (II) described herein, e.g., an AhR inhibitor, such as CB7993113 and CMLD-2166, or a non-constitutive AhR agonist, such as CB7950996, and one or more other therapeutic agents, or administration of a therapeutic composition or formulation comprising an AhR inhibitor or non-constitutive AhR agonist as described herein, results in reduction or inhibition of the cancer as described herein. A "therapeutically synergistic amount" is that amount of a small molecule AhR modulator of Formula (I) or Formula (II) described herein, e.g., an AhR inhibitor, such as CB7993113 and CMLD-2166, or a non-constitutive AhR agonist, such as CB7950996, and one or more other therapeutic agents necessary to synergistically or significantly reduce or eliminate conditions or symptoms associated with a particular cancer.

In some embodiments, a small molecule AhR modulator of Formula (I) or Formula (II) described herein, e.g., an AhR inhibitor, such as CB7993113 and CMLD-2166, or a non-constitutive AhR agonist, such as CB7950996, and one or more other therapeutic agents can be administered simultaneously or sequentially in an amount and for a time sufficient to reduce or eliminate the occurrence or recurrence of a tumor, a dormant tumor, or a micrometastases. In some embodiments, the small molecule AhR modulators of Formula (I) or Formula (II) described herein, e.g., an AhR inhibitor, such as CB7993113 and CMLD-2166, or a non-constitutive AhR agonist, such as CB7950996, and one or more other therapeutic agents can be administered as maintenance therapy to prevent or reduce the likelihood of recurrence of the tumor.

As will be understood by those of ordinary skill in the art, the appropriate doses of chemotherapeutic agents or other anti-cancer agents will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

In addition to the above therapeutic regimes, the subject can be subjected to radiation therapy.

The term "anti-cancer therapy" refers to a therapy useful in treating cancer. Examples of anti-cancer therapeutic agents include, but are limited to, e.g., surgery, radiation therapy, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin™), anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, B1yS, APRIL, BCMA or VEGF receptor(s), TRAIL/Apo2, and other bioactive and organic chemical agents, etc. Combinations thereof are also included in the embodiments described herein.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

As used herein, a "chemotherapeutic agent" is a chemical compound useful in the treatment of cancer. Examples of chemotherapeutic agents include, but are not limited to, alkylating agents such as thiotepa and CYTOXAN™ cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™, polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™, paclitaxel (Bristol-Myers Squibb Oncology, Princeton, N.J.), ABRAXANE™, Cremophor-free, albumin-engineered nanoparticle formulation of paclitaxel (American Pharmaceutical Partners, Schaumberg, Ill.), and TAXOTERE™, doxetaxel (Rhone-Poulenc Rorer, Antony, France); chloranbucil; GEMZAR™ gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb™); inhibitors of PKC-alpha, Raf, H-Ras, EGFR (e.g., erlotinib (Tarceva™.)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE™ megestrol acetate, AROMASIN™ exemestane, formestanie, fadrozole, RIVISOR™ vorozole, FEMARA™ letrozole, and ARIMIDEX™ anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Ralf and H-Ras; ribozymes such as a VEGF expression inhibitor (e.g., ANGIOZYME™ ribozyme) and a HER2 expression inhibitor; vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL™, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13.

The term "prodrug" as used herein refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, .beta.-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

This invention is further illustrated by the following examples which should not be construed as limiting.

EXAMPLES

Binding and activation of the aryl hydrocarbon receptor (AhR) is the proximal signaling event through which classes of ubiquitous environmental pollutants initiate mammary tumorigenesis. The inventors have demonstrated that AhR also plays an important role in later stages of tumorigenesis by regulating tumor growth and invasion. Inhibition of constitutive AhR activity through molecular or biochemical means was found to significantly reduce immortalized tumor growth and invasion in multiple in vitro assays. Notably, the inventors found that this AhR-mediated tumor progression occurs in the absence of environmental AhR ligands and is relevant to virtually all mammary tumors, including "spontaneous" tumors not induced by environmental chemicals. The data further indicates that AhR appears to play a similar role in most solid cancers. Consequently, described herein are AhR inhibitors and non-constitutive AhR agonists and for use as therapeutics for reducing tumor growth, invasion and metastasis. Described herein are novel targeted therapeutics for treatment of breast cancer at any stage. In some embodiments, these novel targeted therapeutics are particularly useful in patients that have failed conventional non-targeted chemotherapeutics or Her2/neu-, ER-, or PR-dependent therapeutics.

High throughput screening of over 4000 compounds identified several AhR modifiers, including both AhR inhibitors and non-constitutive AhR agonists, at least three of which inhibit tumor invasion. Hit-to-lead chemistry can be employed using the novel biologic assays of tumor aggressiveness described herein to develop a set of highly potent and specific AhR inhibitors for evaluation in preclinical animal studies. Using shape- and eletrostatics-based screening, scaffold hopping, and computational medicinal chemistry AhR inhibitors and non-constitutive AhR agonists can be identified in commercial chemical libraries. Such AhR inhibitors and non-constitutive AhR agonists can be evaluated by HTS and, in an iterative process, chemically altered to produce ligands with improved AhR-binding affinity, potency, stability, and solubility. Novel synthetic AhR inhibitors and non-constitutive AhR agonists can be evaluated using the secondary breast tumor growth and invasion assays described herein prior to in vitro toxicity, specificity, stability, and absorption testing. The synthetic AhR inhibitors and non-constitutive AhR agonists described herein can be used in be the synthesis of lead compounds that significantly block tumor progression in vitro and are exhibit a high level of efficacy and specificity in preclinical animal testing. The synthetic AhR inhibitors and non-constitutive AhR agonists are useful in the treatment of advanced breast cancers, as a preventative for high risk patients, and are applicable for treatment of a variety of solid tumors.

Background

Figure 2:
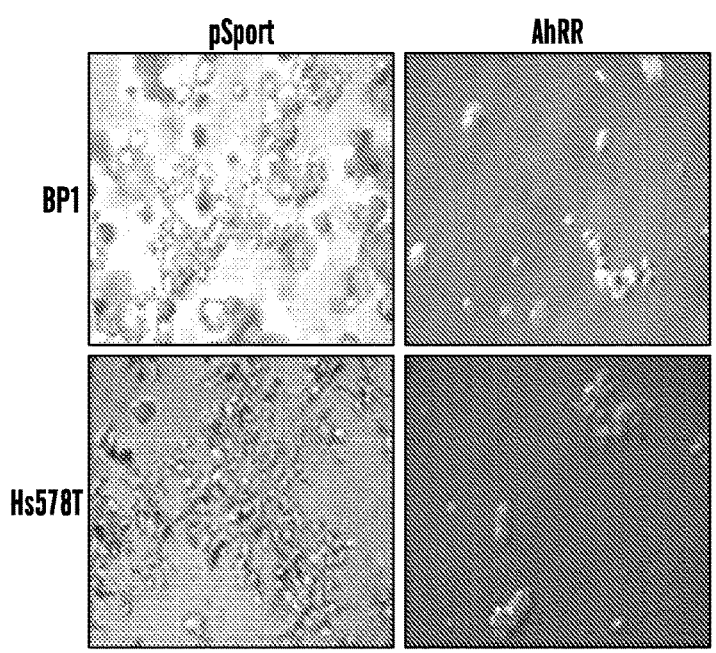
FIG. 2 demonstrates that AhR inhibition with AhRR inhibits tumor invasion in matrigel.
Figure 3:
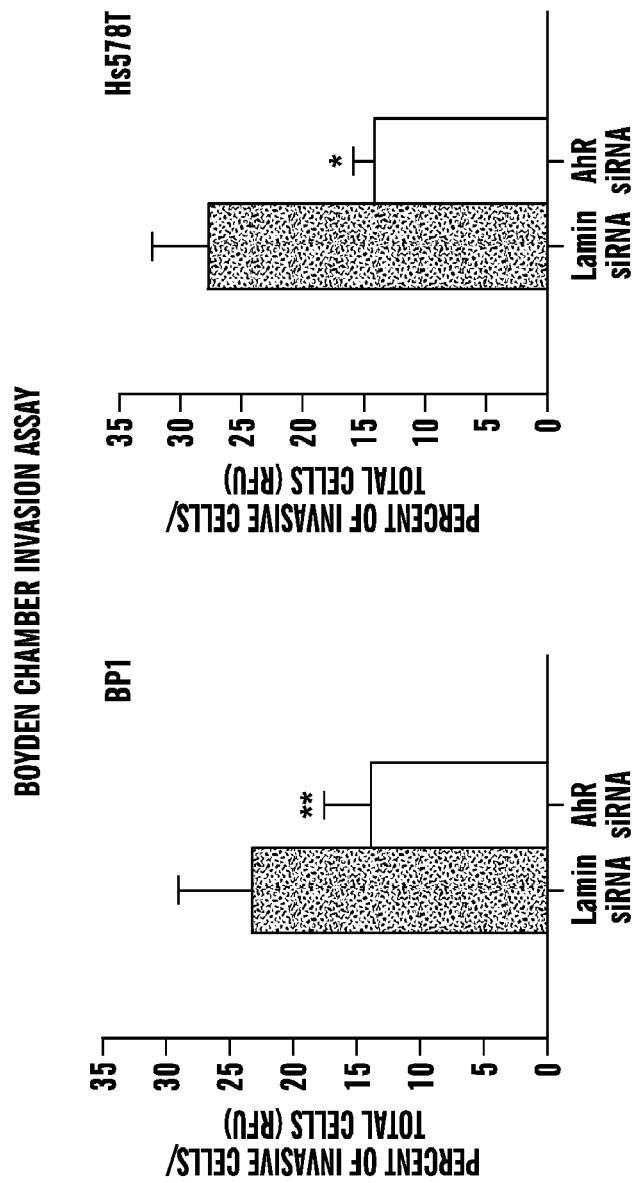
FIG. 3 demonstrates that AhR downregulation with AhR siRNA inhibits invasion in Boyden Chambers. The number of cells above and below the Matrigel¬ containing membrane was determined after 48 hrs and the percentage of cells in the lower chamber calculated. *p<0.04; **p<0.03.

Ubiquitous AhR ligands initiate mammary tumorigenesis by activating aryl hydrocarbon receptor/transcription factor. In normal cells, the cytosolic AhR can be "activated" by pollutants such as dioxins, non-ortho substituted polychlorinated biphenyls, and polycyclic aromatic hydrocarbons, resulting in AhR translocation to the nucleus and gene regulation. The inventors investigate the activation and function of this receptor/transcription factor in malignant cells, and were the first to demonstrate a remarkable 50-fold increase in AhR mRNA in rat mammary tumors relative to normal tissue (2), in contrast to other studies that describe acute toxicological outcomes of AhR activation in normal cells. The inventors have identified AhR over-expression in mouse mammary tumors, human and mouse tumor lines, and primary human mammary tumors (3-15). The inventors demonstrated in all of these systems that the AhR is constitutively active in the absence of environmental stimuli, indicating that the AhR contributes to mammary cancer initiation, growth, and invasion. Other data correlates constitutive AhR transcriptional activity with tumor growth rates and invasiveness, and with up-regulated oncogenes associated with tumor growth and invasion (9, 12, 16), and by the direct demonstration that AhR knock down by molecular techniques inhibits immortalized cell growth (through p21 up-regulation) and tumor invasion in vitro (8, 12, 14, 17) (FIGS. 1-3). Given what is known of AhR biology and the large therapeutic window afforded by AhR hyperexpression in tumors, mechanism-based toxicity is a decreased risk, and AhR inhibitors and non-constitutive AhR agonists can be protective for individuals at high risk because of genetic predispositions or environmental exposures.

Results

Figure 4A:
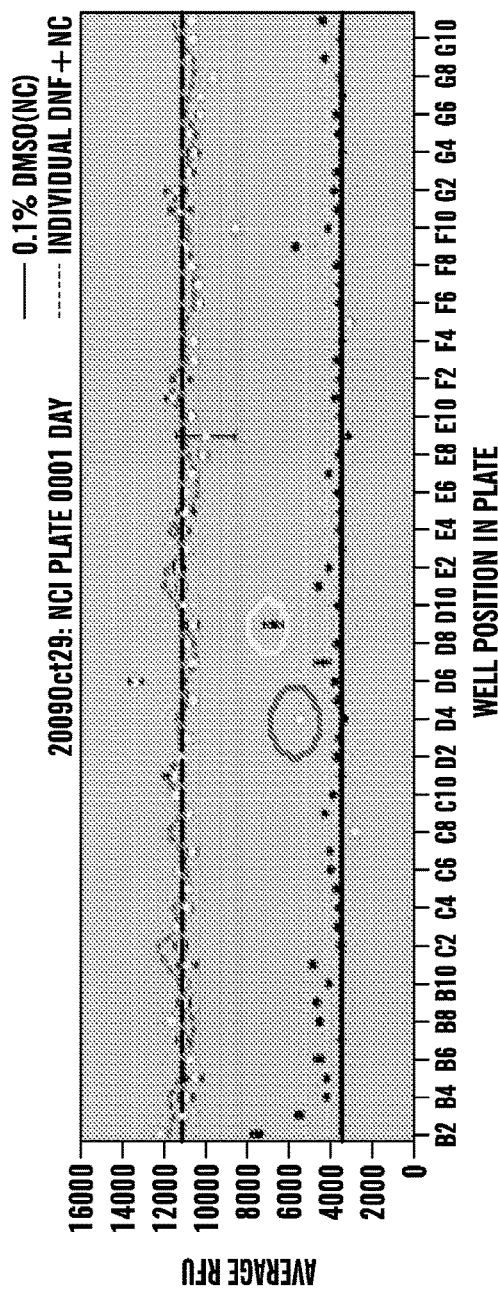
FIGS. 4A-4B show that high-throughput screening (HTS) for AhR agonists and antagonists.
Figure 4B:
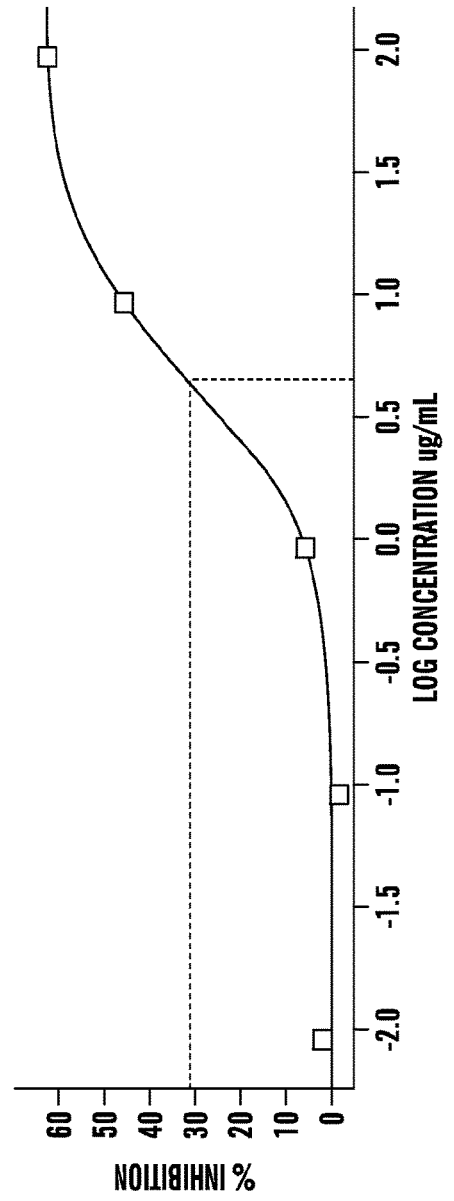

Using a high throughput reporter-based AhR bioassay and cell viability assay, over 4000 CMLD compounds, FDA drugs, and NCI-generated extracts were screened, and 8 non-toxic AhR inhibitors (2 from the CMLD) and 19 AhR agonists (14 from the CMLD) were identified (as shown in, e.g., FIGS. 4A-4B). $IC_{50}$ values for inhibitors and $EC_{50}$ values for agonists were determined (Table 1). One of these discovered inhibitors (CMLD-2166), its enantiomer (CMLD-2186), and a previously described lipid soluble AhR inhibitor (CH223191) blocked tumor growth and invasion (FIGS. 5A-5B and 7A-7B).

To determine whether the inhibitory action of CB7993113 involves binding to the AhR and blocking its translocation to the nucleus, Hepa-1 cells were treated with 1-10 uM CB7993113. One hour later they were challenged with a strong AhR agonist and prototypic PAH, DMBA (1 uM). After a 30 minute incubation period, cells were harvested and extracts from cell nuclei and cytoplasm were obtained. These extracts then were probed for levels of AhR and, as a loading control, β-actin, by western immunoblotting.

Figure 6:
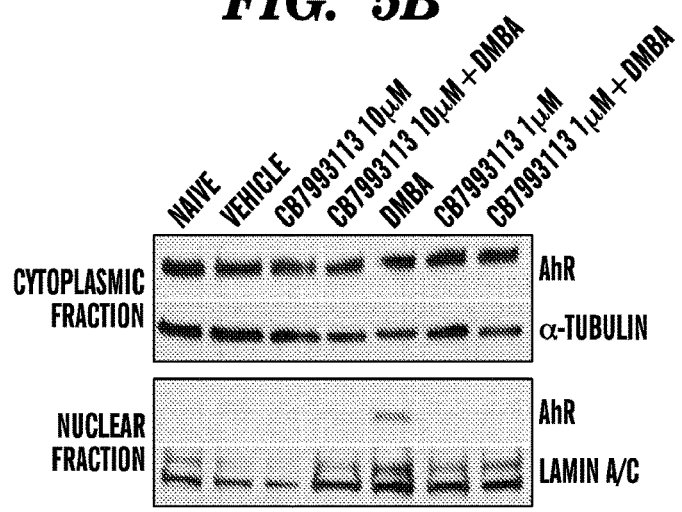
FIG. 6 demonstrates that CB7993113 blocks translocation of the AhR to the nucleus after stimulation of cells with DMBA, an AhR agonist. Hepa-1 cells were treated with vehicle or 1-10 μM CH223191. One hour later cells were treated with 0.1 μM DMBA (where indicated) and incubated for 30 minutes. Cells were harvested and proteins from the cytoplasm and nuclei were extracted. Extracted proteins were subjected to AhR- or, as loading control, β-actin-specific western immunoblots. Data are representative of 3 independent experiments.

As can be seen from FIG. 6, treatment of cells with the AhR inhibitor alone had no effect on translocation of the AhR to the nucleus (lanes 3 and 6) confirming the lack of AhR agonist activity. In contrast, treatment with DMBA alone significantly induced nuclear translocation (lane 5). Addition of 1-10 uM CB7993113 completely blocked DMBA-induced AhR translocation (lanes 4 and 7). These results are consistent with the hypothesis that CB7993113, and similar competitive AhR inhibitors, block AhR transcriptional activity by preventing translocation of the AhR to the nucleus.

Figure 8A:
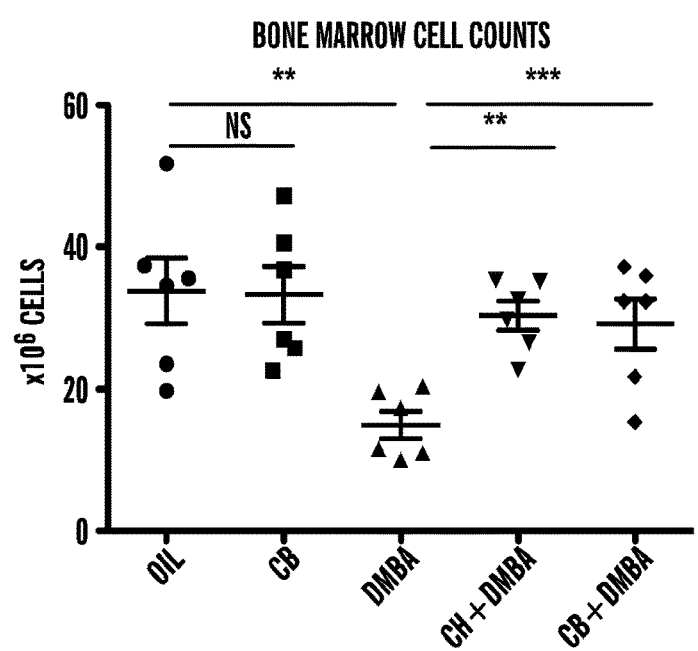
FIGS. 8A-8B demonstrate that CB7993113 is capable of blocking acutely toxic effects of a potent AhR ligand and prototypic PAH, DMBA, in vivo, and that three subpopulations of bone marrow cells affected by DMBA are all rescued by treatment with CB7993113.

To test the ability of one of the lead compounds described herein, CB7993113, to be absorbed and to function effectively in vivo, C57BL/6 mice were treated with an acutely toxic dose (50 mg/kg) of DMBA, a potent AhR agonist, in the presence or absence of CB7993113 or another AhR inhibitor, CH223191. We had previously demonstrated that treatment of mice with 50 mg/kg DMBA induces a rapid loss (within 48 hours) of bone marrow hematopoietic cells. These studies were confirmed here by demonstrating that DMBA treatment resulted in a significant decrease in the total number of bone marrow cells 48 hours after i.p. injection of DMBA (FIG. 8A). This decrease in the total number of bone marrow cells was prevented by the i.p. injection of 50 mg/kg CH223191 or CB7993113.

Figure 8B:
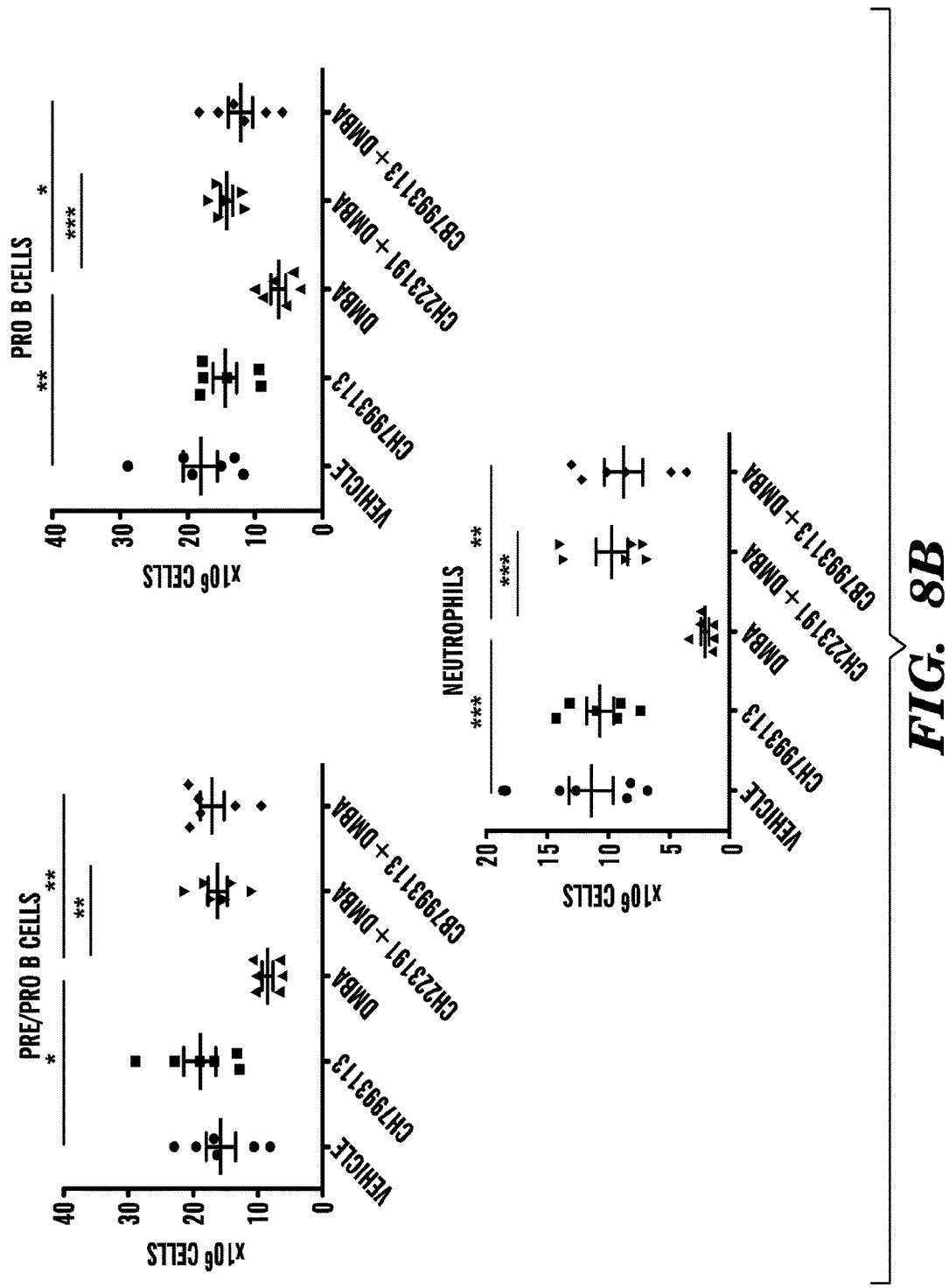

Furthermore, previous experiments were extended by demonstrating that acute treatment with DMBA resulted in the specific loss of pro B cells, pre B cells, and neutrophils (FIG. 8B). Importantly, co-administration of either CH223191 or CB7993113 completely blocked this decrease in pro B cells, pre-B cells sells, and neutrophils. These are important findings since they demonstrate that the AhR inhibitors described herein are absorbed in vivo, and that pharmacologically effective doses can be reached in peripheral organs such as the bone marrow.

TABLE 1

AhR Agonist/Antagonist Potency

| AhR Antagonists | $IC_{50}$ |
|---|---|
| CH223191 | 0.33 μM |
| CMLD 2186 | 0.20 μM |
| CMLD 2186 | NT |
| NCI 1D4 | 4.44 μg/ml |
| NCI 4B2 | 8.83 μg/ml |

| AhR Agonists | $EC_{50}$ |
|---|---|
| CMLD 001815, plate 4, C3 | >10 μM |
| Agonist - 2190, Plate 4, F5 | 3.5 μM |
| CMLD G14, Plate 6, B9 | 5.32 μM |
| CMLD 216, Plate 6, G8 | 3.83 μM |
| CMLD 4262, Plate 9, E5 | >10 μM |
| CMLD 4878, Plate 15, B5 | >10 μM |
| CMLD 5352, Plate 15, D4 | >10 μM |
| CMLD 2168, Plate 25, C5 | >10 μM |
| CMLD 5354, Plate 28, E6 | >10 μM |
| CMLD 05854, Plate 3D, D4 | 3.95 μM |

Compounds shown in the high throughput screen to inhibit or to induce the AhR without affecting the viability of the test cell line were titered in the absence (agonists) or presence (antagonists) of 1 μM BNF, a known AhR agonist, $IC_{50}$s or $EC_{50}$s were calculated as in FIG. 5.

Having established an initial data set of AhR ligands (Table 1), these chemical structures can be used to predict and ultimately re-design higher activity AhR inhibitors with the goal of generating highly specific and soluble inhibitors effective in the 10-100 nanomolar range. To this end, commercial chemical libraries can be screened to identify AhR ligands and then, in an iterative process, chemical characteristics that improve AhR inhibitor potency while maintaining or improving specificity, stability, and solubility can be focused on.

Computational shape- and electrostatics-based scaffold hopping techniques are frequently employed in cases where ligand docking models are not feasible due to a lack of X-ray crystallography data (18-22), as is the case with the AhR. To acquire critical chemical structure information required for designing more potent AhR inhibitors, shape-based screening and scaffold hopping can be applied to identify additional novel AhR ligands in commercial libraries (see FIG. 9 for exemplary details). Libraries containing over 700,000 compounds are available from ASDI and ChemBridge. These libraries represent broad coverage of pharmacophore space while maintaining good lead and drug-like properties. The OpenEye program OMEGA v2.2 (23) can be used for this computational approach using our known AhR ligands as a training set. Identification of agonists as well as antagonists is important since agonist structures help define moieties important for AhR binding, while a comparison of agonists and antagonists facilitates identification of residues responsible for receptor inhibition.

Pharmacophore modeling also can be performed as a complementary computational approach. Using the Accelrys Discovery Studio computational package, structures and construct pharmacophores can be imported using our AhR ligand training set. Three-dimensional maps of each structure with associated moiety functionality (e.g., hydrogen bond acceptors/donors, lipophilic regions) can be generated. Candidate compounds can then be re-selected from commercial chemical sets. Though it is likely that non-overlapping hit sets could be identified for screening from the shape-based and pharmacophore modeling, those compounds predicted by both methods can be prioritized for purchase and screening in the high throughput AhR bioassay. Confirmed hits will be titered to establish $IC_{50}/EC_{50}s$. Antagonists can be characterized as competitive versus non-competitive by their ability to displace radiolabeled TCDD as we described (24).

Information gathered from this first round of prediction/testing can be used to custom design higher affinity AhR modifiers. Synthesis of modified, second generation compounds using either a CMLD-BU or commercial compound scaffold can be performed. The synthesized compounds can be evaluated for potency (and toxicity) in the AhR reporter bioassay, modified again as dictated by the empirical results and pharmacophore modeling, and retested in the reporter assay.

Secondary Assays and in Vitro ADMET.

Lead compounds shown to be active but non-toxic in the bioassays can be further scrutinized for possible toxicity using flow cytometry-based vital dyes and a variety of primary human cells and cell lines available to the inventors, including primary human mammary epithelial cells, lymphocytes, and hematopoietic stem cells. Specificity of up to 10 non-toxic lead compounds can be evaluated using ERα-, PPARγ-, and NF-κB-driven reporter assays available to the inventors. Lead compounds then can be comprehensively screened for off-target effects using the TransAm commercial transcription factor array from Active Motif. To confirm AhR inhibition in human mammary tumor cells, lead compounds can be titered into cultures of BP1 and Hs578T human mammary tumor cells, and inhibition of nuclear AhR translocation assayed as described (24). Compound CMLD-21 66, shown to inhibit tumor invasion (FIGS. 7A-7B), can be used as a positive control. Compounds inhibiting constitutive AhR nuclear translocation then can be evaluated in secondary assays for inhibition of tumor growth ($^3$H-thymidine incorporation) and invasion (morphology in Matrigel and migration in Boyden Chambers), as described herein (see FIGS. 5A-5B and 7A-7B).

Having established potency, toxicity, specificity, and efficacy in vitro, further Absorption, Distribution, Metabolism, Excretion, and Toxicity (ADMET) analyses of lead compounds can be outsourced to companies, such as for example, Apredica, Inc. Among other outcomes, parameters that can be evaluated include, but are not limited to: 1) compound permeability using Caco-2 monolayers to predict human oral bioavailability; 2) metabolic breakdown in the presence of liver microsomes or mouse/human plasma; and 3) stability in the presence of gastric and intestinal fluids. In addition, experimental measurement of compound solubility can be employed to complement the computed values utilized during the compound design and optimization cycles.

The studies described herein are useful for advancing product development from the biologic discovery to the lead optimization phase. In addition, in vivo pharmacokinetic and efficacy studies can be performed using, for example, a human mammary tumor xenograft model to quantify tumor growth and metastasis in live mice in real time in 3 dimensions (25, 26).

In the U.S., the age-adjusted incidence of breast cancer increased ~1% per year between 1940 and 1990 (27, 28) and 0.4%/year between 1987 and 2002 (29), potentially, without wishing to be bound or limited by a theory, due to exposures to environmental carcinogens including AhR ligands (30-33). Breast cancer is now the second most common cancer (after skin cancer) in women, with 225,000 new U.S. cases and 40,000 breast cancer-related deaths per year. One in 8 women born this year will be diagnosed with breast cancer in their lifetime (34). The total number of women diagnosed with breast cancer is likely to grow significantly over the next 20 years as the demographics of the population shift towards an older population (34). Thus, even subsets of breast cancer patients served by a targeted therapeutic such as those described herein represent a relatively large population.

While appropriate as targeted therapeutics for all breast cancer patients, the compounds described herein can be targeted towards patients with aggressive "triple negative" breast cancers, for example, those patients that have failed conventional chemotherapy or Her2/neu-, ER-, or PR-dependent therapeutics, since constitutive AhR activity increases with, and likely contributes to increasing levels of tumor aggressiveness (8). As the small molecule compounds of Formula (I) and Formula (II) described herein are useful as targeted therapeutics directed specifically at a protein (the AhR) expressed at extremely high levels in cancers, and because AhR modifiers are not expected to be associated with significant mechanism-based toxicities, in some embodiments, the small molecule compounds of Formula (I) and Formula (II) can be used, for example, as an adjuvant (e.g., post-surgical) therapeutic for patients desiring a non-toxic alternative for improved quality of life, or for patients requiring targeted therapeutics because of accumulated organ toxicity.

In addition to contributing to end stage tumor progression, the studies described herein and in rat and mouse models of mammary tumorigenesis indicate that the AhR plays a role early in tumorigenesis prior to overt tumor formation (2-4, 8, 13). Therefore, in some embodiments, AhR therapy using the small molecule compounds of Formula (I) and Formula (II) described herein can be used as a long-term preventative for women at high risk of breast cancer. For example, in some embodiments, the compounds described herein are used as prophylactic therapeutics in women at high or increased genetic or environmental risk for breast cancer due to inheritance of mutated BRCA1, BRCA2, CHEK2, ATM, BRIP1, or PALB2 genes, family histories of reproductive organ cancers, or chronic exposures to environmental carcinogens (36). In other embodiments, the small molecule compounds of Formula (I) and Formula (II) described herein can be used as long-term preventatives for the 42,000 high risk women diagnosed each year with pre-cancerous lesions (ductal carcinoma in situ/DCIS), most of whom will develop invasive adenocarcinomas (37). Importantly, the studies described herein further indicate that the AhR is hyper-expressed and constitutively active in virtually all cancer types, including other epithelial tumors such as prostate, lung, and pancreatic ductal cell carcinomas. Accordingly, in some embodiments, the compounds described herein can be used in the treatment of cancer.

FIG. 1 shows that AhR inhibition with AhRR upregulates p21 and decreases MCF-10F growth. MCF-10F cells were stably transduced with lentivirus vectors encoding GFP or GFP and AhR repressor (AhRR) to suppress AhR activity. AhRR-GFPlow and AhRR-iGFPhigh cells were selected by flow cytometry. Cells were plated at equal numbers and cell numbers determined 1-6 days later. Insert: p21 protein levels in control or AhRR-transduced cells.

FIG. 2 demonstrates that AhR inhibition with AhRR inhibits tumor invasion in matrigel. Malignant BP1 and Hs578T cells were transiently transfected with control (pSport) or AhR Repressor plasmids, to suppress AhR activity and plated in Matrigel. Photos were taken 5-7 days later.

FIG. 3 demonstrates that AhR downregulation with AhR siRNA inhibits invasion in Boyden Chambers. Malignant BP1 and Hs578T cells were transiently transfected with control or AhR-specific siRNA and plated in the upper chamber of in serum free medium. Serum-containing medium was added to the lower chamber. The number of cells above and below the Matrigel¬ containing membrane was determined 48 hrs later and the percentage of cells in the lower chamber calculated. *p<0.04; **p<0.03.

FIGS. 4A-4B show high-throughput screening (HTS) for AhR agonists and antagonists. FIG. 4A shows H1G1 cells expressing an AhR-driven GFP reporter construct were plated into 384 well plates and treated with candidate AhR modifiers alone (dark line) or together with BNF, a known AhR agonist (light line). 24 hours later GFP fluorescence was measured and cells stained for viability. A dark circle identifies an AhR inhibitor while the light circle indicates an agonist. FIG. 4B shows data from the non-toxic compound identified in "A," which was titered in the presence of BNF to calculate the $IC_{50}$. Over 4,000 compounds were screened in this semi-automated assay.

Figure 5A:
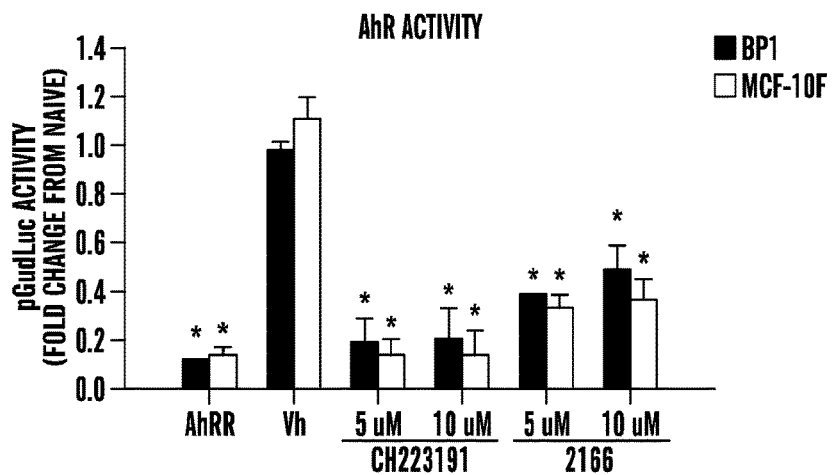
FIGS. 5A-5B demonstrate that CH223191 and CMLD 2166 inhibit constitutive AhR activity and cell growth.
Figure 5B:
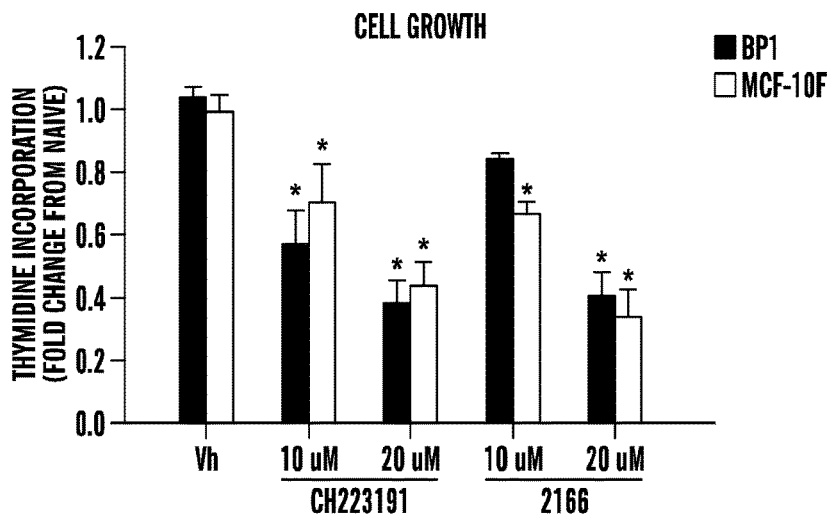

FIGS. 5A-5B demonstrate that CH223191 and CMLD 2166 inhibit constitutive AhR activity and cell growth. FIG. 5A shows data from malignant BP1 and immortalized MCF-10F cells that were transiently transfected with AhR-responsive pGudLuc and treated with vehicle (DMSO), CH2231 91, or 2166. pGudLuc activity was assayed 24 hrs later. FIG. 5B shows data from BP1 and MCF-10F cells that were grown for 18 hrs in the presence of DMSO, CH2231 91, or 2166 and 3H-thymidine incorporation determined. *p<0.05.

FIG. 6 demonstrates that CB7993113 blocks translocation of the AhR to the nucleus after stimulation of cells with DMBA, an AhR agonist. Hepa-1 cells were treated with vehicle or 1-10 µM CH223191. One hour later cells were treated with 0.1 µM DMBA (where indicated) and incubated for 30 minutes. Cells were harvested and proteins from the cytoplasm and nuclei were extracted. Extracted proteins were subjected to AhR- or, as loading control, β-actin-specific western immunoblots. Data are representative of 3 independent experiments.

Figure 7A:
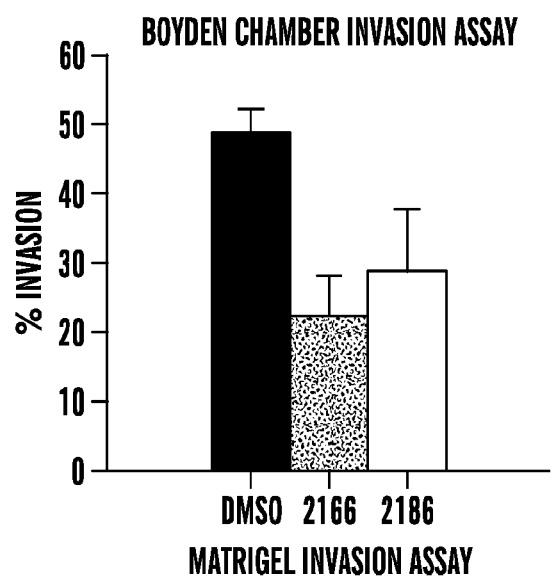
FIGS. 7A-7B demonstrate that CH223191, CMLD-2166 and CMLD-2186 inhibit tumor invasion. Hs578T cells were cultured in Boyden Chambers (FIG. 7A) or in Matrigel (FIG. 7B) in the presence of DMSO, $10^{-5}$M CMLD-2166, CMLD-2186 (a 2166 enantiomer) or CH223191 and assayed for invasion 2 (Boyden Chambers) or 7 (Matrigel) days later.
Figure 7B:
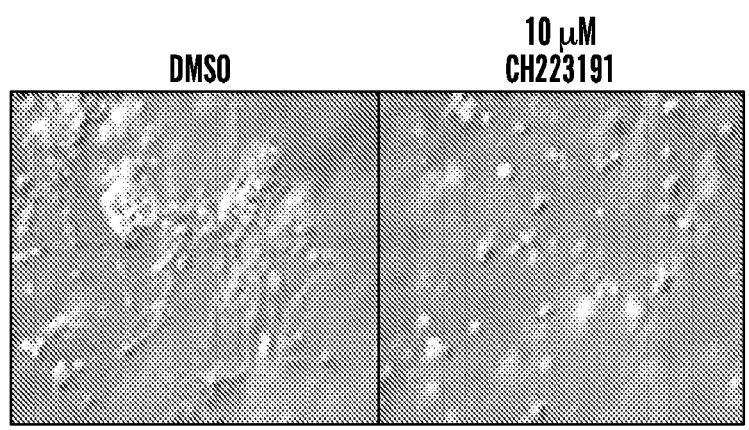

FIGS. 7A-7B demonstrate that CH223191, CMLD-2166 and CMLD-2186 inhibit tumor invasion. Hs578T cells were cultured in Boyden Chambers (FIG. 7A) or in Matrigel (FIG. 7B) in the presence of DMSO, $10^{-5}$M CMLD-2166, CMLD¬ 2186 (a 2166 enantiomer) or CH223191 and assayed for invasion 2 (Boyden Chambers) or 7 (Matrigel) days later.

FIGS. 8A-8B demonstrate that CB7993113 is capable of blocking acutely toxic effects of a potent AhR ligand and prototypic PAH, DMBA, in vivo, and that three subpopulations of bone marrow cells affected by DMBA are all rescued by treatment with CB7993113. FIG. 8A shows data from C57BL/6 mice (6/group) that were injected i.p. on day −1 and day 0 with vehicle (oil) or 50 mg/kg CB7993113. Mice then were injected with 50 mg/kg DMBA. Mice were sacrificed 48 hours later. Bone marrow hematopoietic cells were expunged from the bone and viable cells counted. Data are presented as the average number of viable white blood cells+SE. p<0.01, *P<0.001, student's t-test. FIG. 8B confirms the data shown in FIG. 8A and further demonstrates that the three subpopulations of bone marrow cells affected by DMBA are all rescued by treatment with CB7993113. C57BL/6 mice (6/group) were treated as in FIG. 8A. The percentage and number of viable bone marrow pro B cells, pre B cells, and neutrophils were determined 48 hours later by flow cytometry. Data are presented as the average number of viable cells of each subtype+SE. (*p<0.05, **P<0.01, student's t-test).

Figure 9:
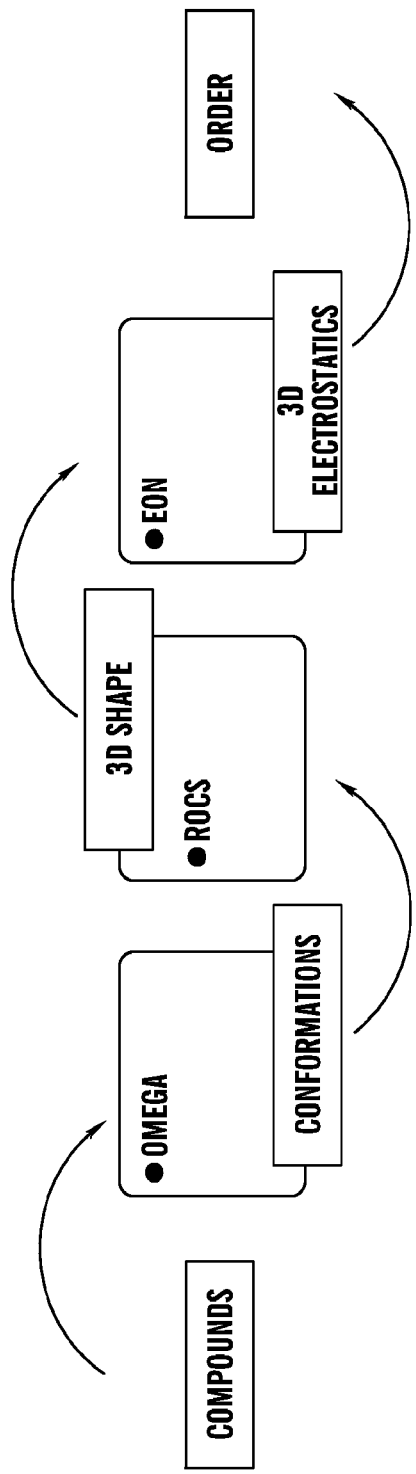
FIG. 9 depicts computational strategies for shape- and electrostatic similarity searching.

FIG. 9 depicts computational strategies for shape- and electrostatic similarity searching. The SMILES strings can be expanded into a 3D conformer database using the OpenEye program OMEGA (v.2.2.1), allowing an energy window of 8 kcal/mol above ground state and a msd cutoff of 0.8 Å per the method described in (1). The maximum rotatable bonds for these experiments is by 16. In order to speed this computation, a fragment library can be pre-generated using the program makefragmentlib. The 3D conformer database then can be searched using ROCS (v.2.3.1), queried against the top 20 lowest energy conformations of the most potent HTS hits, determined using OMEGA. The shape comparison program ROCS can be run using a built-in color force field and hits can be ranked on the basis of the sum of their shape Tanimoto and the color score (known as the "combo score"). The highest scoring overlaps from ROCS can be subjected to electrostatic overlap comparison using EON. For hit list ranking, the electrostatic Tanimoto combo score can be used for ranking. This is the sum of the shape Tanimoto and the Poisson-Boltzman electrostatic Tanimoto. The top 200 compounds from each commercial set can be procured and screened in the high throughput AhR functional assays.

Figure 10:
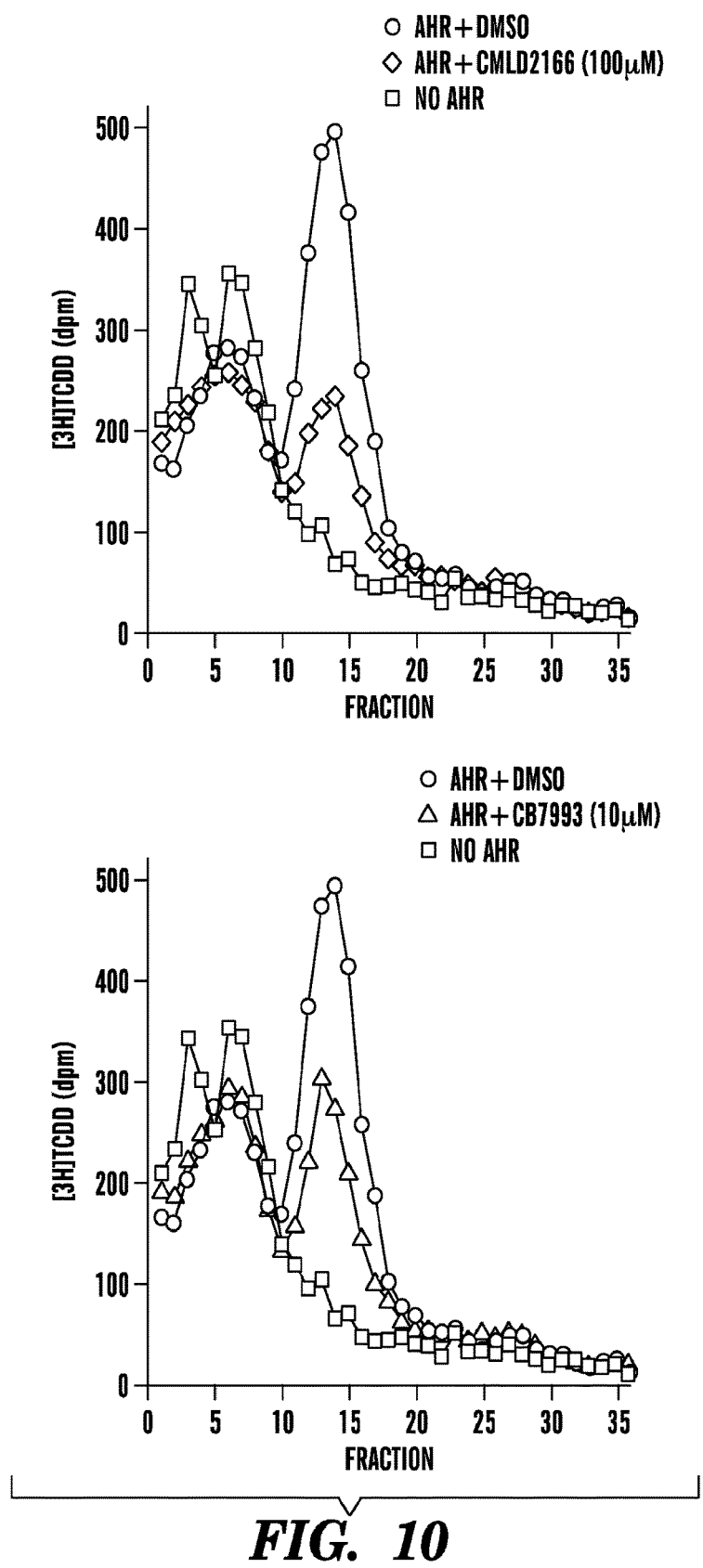
FIG. 10 demonstrates that compounds CMLD-2166 and CB7993113 bind human AhR. The compounds CMLD-2166 and CB7993113 were mixed with in vitro translated human AhR and radiolabeled TCDD (dioxin), a high affinity AhR ligand. Complexes then were separated on a sucrose gradient and fractions assayed for radioactivity. A decrease in the signal (displacement of radiolabeled TCDD) can be seen in fractions 13-16 indicating binding of the test compound to the AhR and displacement of TCDD. These results demonstrate that these compounds are competitive AhR inhibitors.

FIG. 10 demonstrates that compounds CMLD-2166 and CB7993113 bind human AhR. The compounds CMLD-2166 and CB7993113 were mixed with in vitro translated human AhR and radiolabeled TCDD (dioxin), a high affinity AhR ligand. Complexes then were separated on a sucrose gradient and fractions assayed for radioactivity. A decrease in the signal (displacement of radiolabeled TCDD) can be seen in fractions 13-16 indicating binding of the test compound to the AhR and displacement of TCDD. These results demonstrate that these compounds are competitive AhR inhibitors.

Figure 11:
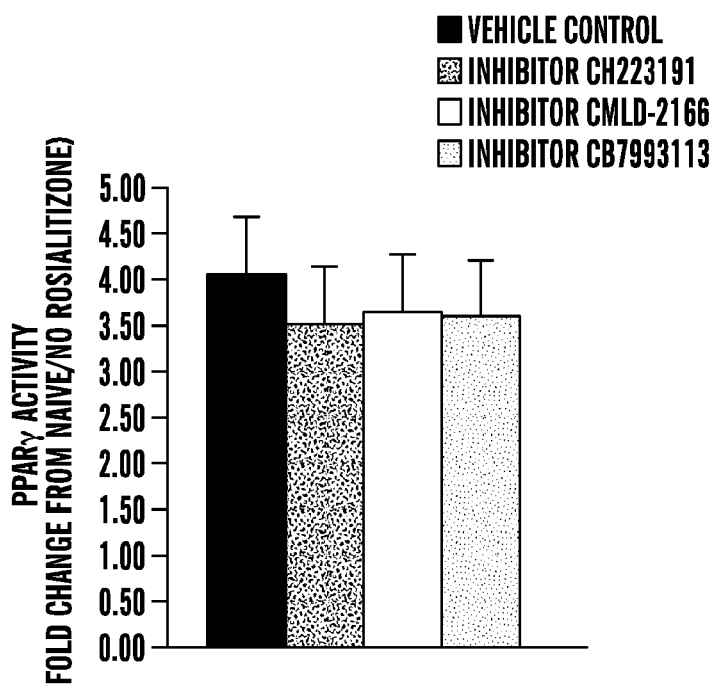
FIG. 11 demonstrates that AhR inhibitors do not significantly block PPARγ-mediated transcription. Data were pooled from 4 experiments Unlike their ability to block AhR-driven reporter activity, the AhR inhibitors had no effect on the PPARγ-driven reporter activity.

FIG. 11 demonstrates that AhR inhibitors do not block PPARγ-mediated transcription. Cos7 cells were transfected with the peroxisome proliferator activator receptor-γ (PPARγ), its dimerization partner, RXR, a PPARγ-driven luciferase reporter construct, and a control CMV-driven GFP reporter for 24 hours. Cells then were treated with a vehicle, 10 μM AhR inhibitor CH223191, 50 μM AhR inhibitor CMLD-2166, or 10 μM AhR inhibitor CB7993113. (These represent high AhR inhibitor doses). Rosiglitazone (1 μM), a strong PPARγ agonist, was added 1 hour later and cells assayed 18-24 hrs thereafter for PPARγ-driven reporter activity (luciferase intensity), normalized to the GFP signal. Data were pooled from 4 experiments. Unlike their ability to block AhR-driven reporter activity, the AhR inhibitors had no effect on the PPARγ-driven reporter activity.

Figure 12:
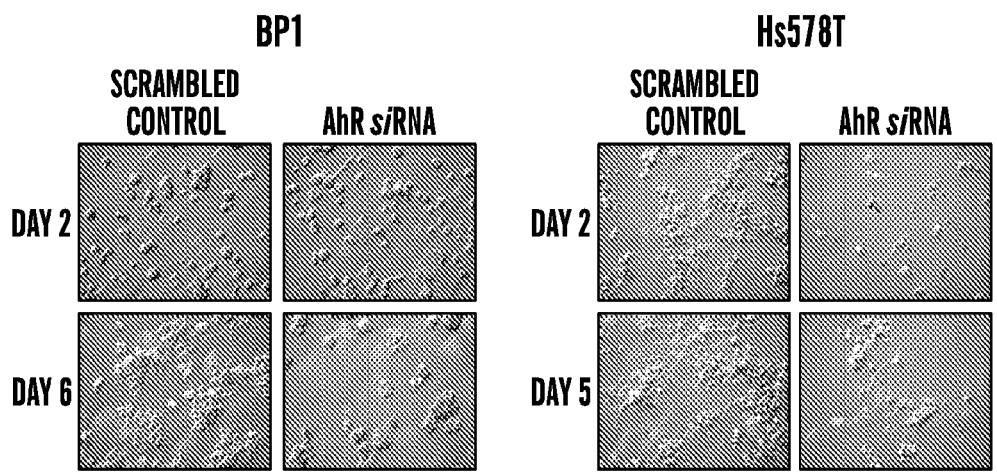
FIG. 12 demonstrates that AhR siRNA transfection blocks tumor invasion in matrigel. BP1 or Hs578T human mammary tumor cells were transiently transfected with control siRNA or AhR siRNA to knock down AhR expression and cells were cultured in Matrigel for 6 days. Shown are colonies of tumor cells that grow from single cells during those 6 days.

FIG. 12 demonstrates that AhR siRNA transfection blocks tumor invasion in matrigel. BP1 or Hs578T human mammary tumor cells were transiently transfected with control siRNA or AhR siRNA to knock down AhR expression and cells were cultured in Matrigel for 6 days. Shown are colonies of tumor cells that grow from single cells during those 6 days.

Figure 13:
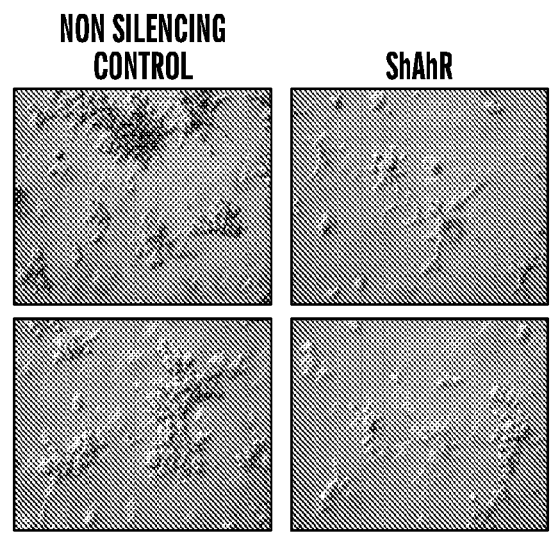
FIG. 13 demonstrates that doxycycline-inducible AhR shRNA blocks tumor invasion in matrigel. Hs578T cells were stably transduced with doxycyline-inducible control (scrambled/non-silencing) shRNA (left) or AhR-specific shRNA (right). Cells were treated with doxycyline to activate both control and AhR shRNA vectors and cells were cultured in Matrigel for 5 days.

FIG. 13 demonstrates that doxycycline-inducible AhR shRNA blocks tumor invasion in matrigel. Hs578T cells were stably transduced with doxycyline-inducible control (scrambled/non-silencing) shRNA (left) or AhR-specific shRNA (right). Cells were treated with doxycyline to activate both control and AhR shRNA vectors and cells were cultured in Matrigel for 5 days.

Figure 14:
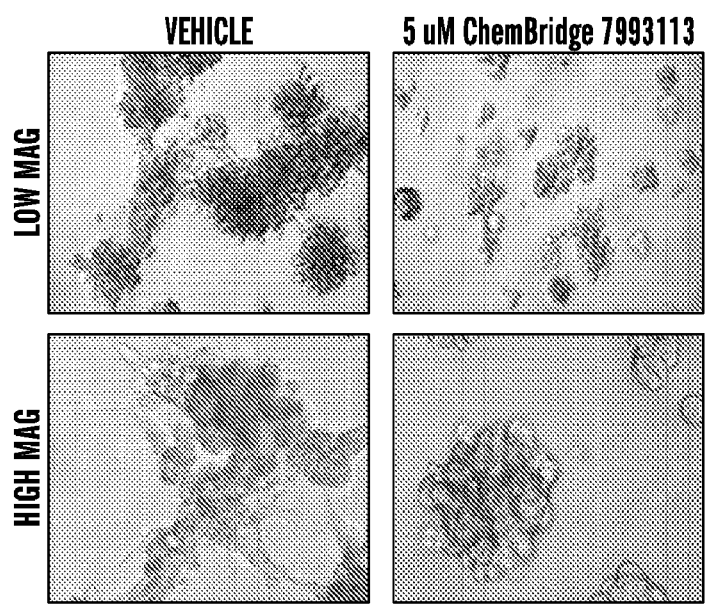
FIG. 14 demonstrates that AhR Inhibitor CB993113 blocks BP1 tumor invasion in matrigel. BP1 cells were cultured in the presence of vehicle (left) or 5 uM CB7993113 in Matrigel for 5 days. CB7993113 is not toxic at the highest doses tested, 10 uM.

FIG. 14 demonstrates that AhR Inhibitor CB993113 blocks BP1 tumor invasion in matrigel. BP1 cells were cultured in the presence of vehicle (left) or 5 uM CB7993113 in Matrigel for 5 days. CB7993113 is not toxic at the highest doses tested, 10 uM.

Figure 15:
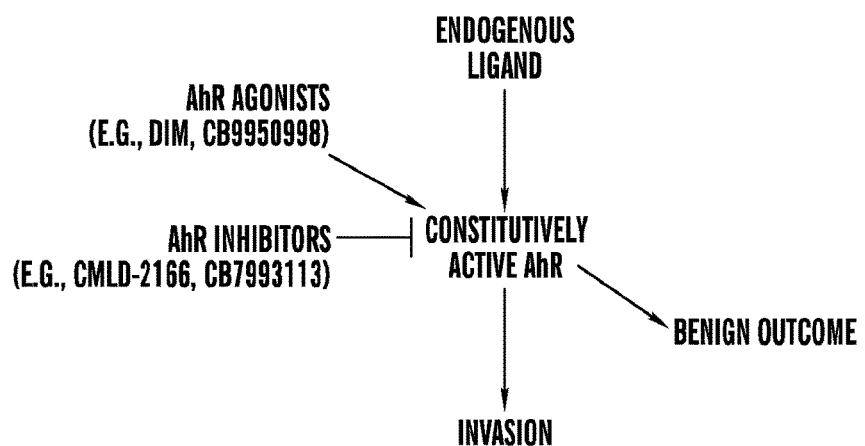
FIG. 15 is a schematic depicting how AhR inhibitors and non-competitive agonists can inhibit tumor invasion.

FIG. 15 is a schematic depicting how AhR inhibitors and agonists can inhibit tumor invasion.

Figure 16A:
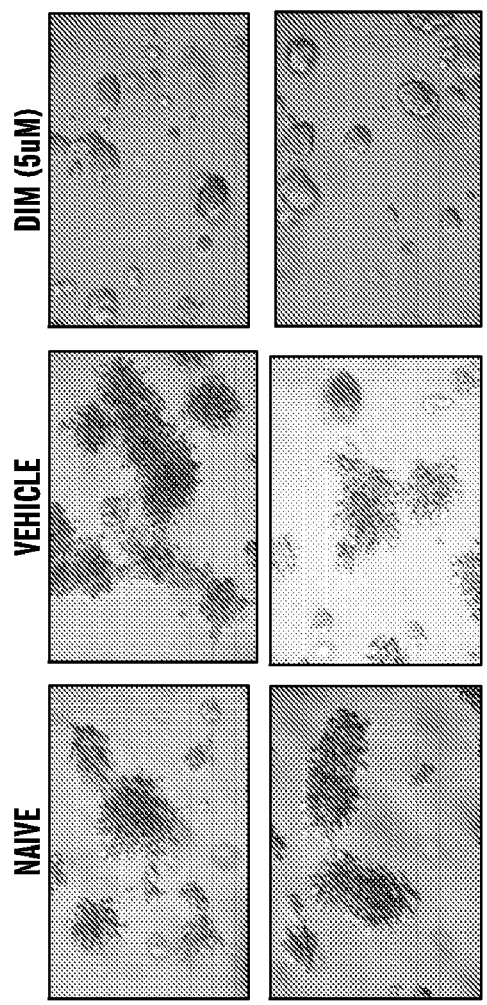
FIGS. 16A-16B demonstrate that AhR agonists reduce human mammary tumor cell (BP1) invasion in matrigel. BP1 cells were cultured in Matrigel in the presence of vehicle, 5 uM DIM (16A), vehicle or 5 uM CB7950998 (16B) for 5 days.
Figure 16B:
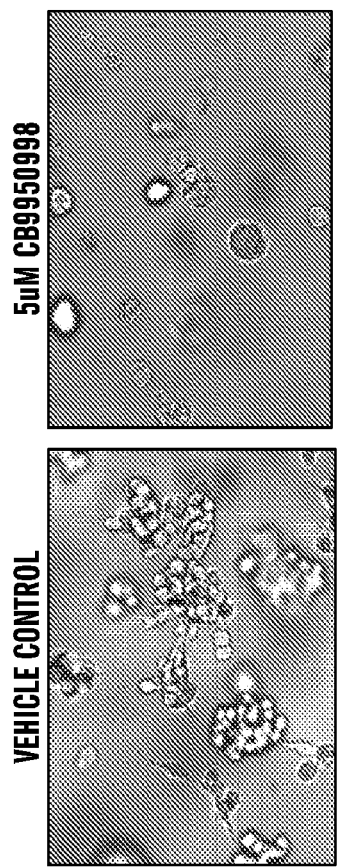

FIGS. 16A-16B demonstrate that AhR agonists reduce human mammary tumor cell (BP1) invasion in matrigel. BP1 cells were cultured in Matrigel in the presence of vehicle, 5 uM DIM (16A), vehicle or 5 uM CB7950998 (16B) for 5 days.

Without wishing to be bound or limited by a theory, the data described herein also indicate that some constitutive AhR agonists up-regulate CYP1A1 and CYP1B1 expression, both of which are associated with increased human breast, ovarian, and lung cancer risk (36, 39-44).

REFERENCES

1. Hawkins, P. C., A. G. Skillman, and A. Nicholls. 2007. Comparison of shape-matching and docking as virtual screening tools. J Med Chem 50:74-82.
2. Trombino, A. F., R. A. Matulka, S. Yang, L. J. Hafer, A. E. Rogers, P. Tosselli, D. Kim, G. E. Sonenshein, R. I. Near, and D. H. Sherr. 2000. Expression of the aryl hydrocarbon receptor/transcription factor (AhR) and AhR-regulated CYP1 gene transcription in a rat model of mammary tumorigenesis. Breast Canc. Res. and Treatment 62:117-131.
3. Currier, N., S. Solomon, E. Demicco, D. Chang, M. Farago, H. Ying, I. Dominguez, A. Rogers, G. Sonenshein, R. Cardiff, J. Xiao, D. Sherr, and D. Seldin. 2005. Oncogenic signaling pathways activated in DMBA-induced mouse mammary tumors. Toxicologic Path 33:726.
4. Murray, S. A., S. Yang, E. Demicco, H. Ying, D. H. Sherr, L. J. Hafer, A. E. Rogers, G. E. Sonenshein, and Z. X. Xiao. 2005. Increased expression of MDM2, cyclin D1, and p27(Kip1) in carcinogen-induced rat mammary tumors. J Cell Biochem.
5. Kim, D. W., L. Gazourian, S. A. Quadri, R. Romieu-Mourez, D. H. Sherr, and G. E. Sonenshein. 2000. The RelA NF-kB subunit and the aryl hydrocarbon receptor (AhR) cooperate to transactivate the c-myc promoter in mammary cells *Equal contributions. Oncogene 19:5498-5506.
6. Murray, T. J., X. Yang, and D. H. Sherr. 2006. Growth of a human mammary tumor cell line is blocked by galangin, a naturally occurring bioflavonoid, and is accompanied by down-regulation of cyclins D3, E, and A. Breast Cancer Res 8:R17.
7. Kavanagh, K. T., L. J. Hafer, D. W. Kim, K. K. Mann, D. H. Sherr, A. E. Rogers, and G. E. Sonenshein. 2001. Green tea extracts decrease carcinogen-induced mammary tumor burden in rats and rate of breast cancer cell proliferation in culture. J Cell Biochem 82:387-398.
8. Schlezinger, J., D. Liu, M. Farago, D. Seldin, K. Belguise, G. Sonenshein, and D. Sherr. 2006. A role for the aryl hydrocarbon receptor in mammary gland tumorigenesis. Biological Chemistry 387:1175-1187.
9. Shin, S. R., N. Sanchez-Velar, D. H. Sherr, and G. E. Sonenshein. 2006. 7,12-dimethylbenz(a)anthracene treatment of a c-rel mouse mammary tumor cell line induces epithelial to mesenchymal transition via activation of nuclear factor-kappaB. Cancer Res 66:2570-2575.
10. Narasimhan, S., S. Rolfe, J. Schlezinger, and D. Sherr. 2010. The aryl hydrocarbon receptor influences human mammary tumor cell invasion. Manuscript in preparation.
11. Solomon, S., X. Yang, S, Narasimhan, S. Karchner, M. Hahn, and D. Sherr. 2010. An inhibitory feedback loop mediated by the aryl hydrocarbon receptor and its repressor in human mammary cells. Manuscript in preparation.
12. Belguise, K., S. Guo, S. Yang, A. E. Rogers, D. C. Seldin, D. H. Sherr, and G. E. Sonenshein. 2007. Green tea polyphenols reverse cooperation between c-Rel and CK2 that induces the aryl hydrocarbon receptor, slug, and an invasive phenotype. Cancer Res 67:11742-11750.
13. Yang, X., S. Solomon, L. R. Fraser, A. F. Trombino, D. Liu, G. E. Sonenshein, E. V. Hestermann, and D. H. Sherr. 2008. Constitutive regulation of CYP1 B1 by the aryl hydrocarbon receptor (AhR) in pre-malignant and malignant mammary tissue. J Cell Biochem 104:402-417.
14. Rolfe, S. S., O, Novikov, S, Narasimhan, D. Liu, and D. H. Sherr. 2010. Constitutively active aryl hydrocarbon receptor (AhR) drives immortalized mammary epithelial cell growth through repression of ChK2 and p21 and CYP1 B1 up-regulation. Manuscript in preparation.
15. Yang, X., D. Liu, T. J. Murray, G. C. Mitchell, E. V. Hesterman, S. I. Karchner, R. R. Merson, M. E. Hahn, and D. H. Sherr. 2005. The aryl hydrocarbon receptor constitutively represses c-myc transcription in human mammary tumor cells. Oncogene 24:7869-7881.
16. Min, C., S. F. Eddy, D. H. Sherr, and G. E. Sonenshein. 2008. NF-kappaB and epithelial to mesenchymal transition of cancer. J Cell Biochem 104:733-744.
17. Hahn, M. E., L. L. Allan, and D. H. Sherr. 2009. Regulation of constitutive and inducible AHR signaling: complex interactions involving the AHR repressor. Biochem Pharmacol 77:485-497.

18. Jakobi, A. J., H. Mauser, and T. Clark. 2008. ParaFrag—an approach for surface-based similarity comparison of molecular fragments. Journal of molecular modeling 14:547-558.
19. Low, C. M., I. M. Buck, T. Cooke, J. R. Cushnir, S. B. Kalindjian, A. Kotecha, M. J. Pether, N. P. Shankley, J. G. Vinter, and L. Wright. 2005. Scaffold hopping with molecular field points: identification of a cholecystokinin-2 (CCK2) receptor pharmacophore and its use in the design of a prototypical series of pyrrole- and imidazole-based CCK2 antagonists. Journal of medicinal chemistry 48:6790-6802.
20. Manallack, D. T. 2008. The use of local surface properties for molecular superimposition. Journal of molecular modeling 14:797-805.
21. Tresadern, G., D. Bemporad, and T. Howe. 2009. A comparison of ligand based virtual screening methods and application to corticotropin releasing factor 1 receptor. Journal of molecular graphics & modelling 27:860-870.
22. Vainio, M. J., J. S. Puranen, and M. S. Johnson. 2009. ShaEP: molecular overlay based on shape and electrostatic potential. Journal of chemical information and modeling 49:492-502.
23. http://www.eyesopen.com/products/applications/omega.html.
24. Quadri, S. A., A. N. Qadri, M. E. Hahn, K. K. Mann, and D. H. Sherr. 2000. The bioflavonoid galangin blocks aryl hydrocarbon receptor activation and polycyclic aromatic hydrocarbon-induced pre-B cell apoptosis. Mol Pharmacol 58:515-525.
25. Javed, A., G. L. Barnes, J. Pratap, T. Antkowiak, L. C. Gerstenfeld, A. J. van Wijnen, J. L. Stein, J. B. Lian, and G. S. Stein. 2005. Impaired intranuclear trafficking of Runx2 (AML3/CBFA1) transcription factors in breast cancer cells inhibits osteolysis in vivo. Proc Natl Acad Sci USA 102:1454-1459.
26. Jenkins, D. E., Y. S. Hornig, Y. Oei, J. Dusich, and T. Purchio. 2005. Bioluminescent human breast cancer cell lines that permit rapid and sensitive in vivo detection of mammary tumors and multiple metastases in immune deficient mice. Breast Cancer Res 7:R444-454.
27. Wingo, P. A., T. Tong, and S. Bolden. 1995. Cancer Statistics, 1995. CA Cancer J Clin 45:8-30.
28. Harris, J. R., M. E. Lippman, U. Veronesi, and W. Willett. 1992. Breast cancer. N. Engl. J. Med. 327:319-328.
29. Edwards, B. K., M. L. Brown, P. A. Wingo, H. L. Howe, E. Ward, L. A. Ries, D. Schrag, P. M. Jamison, A. Jemal, X. C. Wu, C. Friedman, L. Harlan, J. Warren, R. N. Anderson, and L. W. Pickle. 2005. Annual report to the nation on the status of cancer, 1975-2002, featuring population-based trends in cancer treatment. J Natl Cancer Inst 97:1407-1427.
30. Dusich, K., F. Sigurson, W. Hall, and A. Dean. 1980. Cancer rates in a community exposed to low levels of creosote components in municipal water. Minn Med. 63:803-806.
31. Morris, J. J., and E. Seifter. 1992. The role of aromatic hydrocarbons in the genesis of breast cancer. Med Hypotheses 38:177-184.
32. DiAugustine, R., and D. Davis. 1993. A holistic approach to breast cancer. Environ. Health Perspect. 101:116-120.
33. Terry, M. B., M. D. Gammon, F. F. Zhang, S. M. Eng, S. K. Sagiv, A. B. Paykin, Q. Wang, S. Hayes, S. L. Teitelbaum, A. I. Neugut, and R. M. Santella. 2004. Polymorphism in the DNA repair gene XPD, polycyclic aromatic hydrocarbon-DNA adducts, cigarette smoking, and breast cancer risk. Cancer Epidemiol Biomarkers Prey 13:2053-2058.
34. 2010. U.S. Surveillance, Epidemiology, and End Results http://seer.cancer.gov/statfacts/html/breast.html.
35. Frost, and Sullivan. 2008. www.Frost.com.
36. Ishibe, N., S. E. Hankinson, G. A. Colditz, D. Spiegelman, W. C. Willett, F. E. Speizer, K. T. Kelsey, and D. J. Hunter. 1998. Cigarette smoking, cytochrome P450 1A1 polymorphisms, and breast cancer risk in the Nurses' Health Study. Cancer Res 58:667-671.
37. Silverstein, M. J., R. Parker, J. C. Grotting, R. J. Cote, and C. A. Russell. 2001. Ductal carcinoma in situ (DCIS) of the breast: diagnostic and therapeutic controversies. Journal of the American College of Surgeons 192:196-214.
38. http://cinicaltrials.gov/ct2/show/NCT01015521?term=aminoflavone&rank=1.
39. Hayes, C. L., D. C. Spink, B C Spink, J. Q. Cao, N. J. Walker, and T. R. Sutter. 1996. 17 beta-¬ estradiol hydroxylation catalyzed by human cytochrome P450 1 B 1. Proc Natl Acad Sci USA 93:9776-9781.
40. Liehr, J. G., and M. J. Ricci. 1996. 4-Hydroxylation of estrogens as marker of human mammary tumors. Proc Natl Acad Sci USA 93:3294-3296.
41. Belous, A. R., D. L. Hachey, S. Dawling, N. Roodi, and F. F. Parl 2007. Cytochrome P450 1B1-mediated estrogen metabolism results in estrogen-deoxyribonucleoside adduct formation. Cancer Res 67:812-817.
42. Watanabe, J., T. Shimad, E. Gillam, T. Ikuta, K. Suemasu, Y. Higashi, O. Gotoh, and K. Kawajiri. 2000. Association of CYP1 B1 genetic polymorphism with incidence to breast and lung cancer. Pharmacogen. 10:25-33.
43. Sellers, T. A., J. M. Schildkraut, V. S. Pankratz, R. A. Vierkant, Z. S. Fredericksen, J. E. Olson, J. Cunningham, W. Taylor, M. Liebow, C. McPherson, L. C. Hartmann, T. Pal, and A. A. Adjei. 2005. Estrogen bioactivation, genetic polymorphisms, and ovarian cancer. Cancer Epidemiol Biomarkers Prey 14:2536-2543.
44. Faraglia, B., S. Y. Chen, M. D. Gammon, Y. Zhang, S. L. Teitelbaum, A. I. Neugut, H. Ahsan, G. C. Garbowski, H. Hibshoosh, D. Lin, F. F. Kadlubar, and R. M. Santella. 2003. Evaluation of 4-aminobiphenyl-DNA adducts in human breast cancer: the influence of tobacco smoke. Carcinogenesis 24:719-725.

We claim:

1. A pharmaceutical composition comprising an aryl hydrocarbon receptor (AhR) modulator according to Formula (Ia) and a pharmaceutically acceptable excipient, carrier or stabilizer:

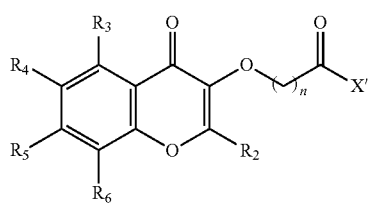

FORMULA (Ia)

wherein:

X' is H, unsubstituted alkyl, aminosulfonyl, acyl, aryl, or heteroaryl, where each of aminosulfonyl, acyl, aryl, or heteroaryl may be optionally substituted;

n is 0-6;

$R_2$ is H, alkyl, acyl, heteroaryl, arylalkyl, cycloalkyl, heteroarylalkyl, heterocyclyl, or haloalkyl, each of which may be optionally substituted;

$R_3$, $R_4$, $R_5$ and $R_6$ are independently H, alkyl, acyl, halo, aryl, or heteroaryl, each of which may be optionally substituted; or a steroisomer or pharmaceutically acceptable salt thereof; and wherein the pharmaceutical composition is formulated as a capsule, pill, caplet or tablet.

2. A pharmaceutical composition comprising an aryl hydrocarbon receptor (AhR) modulator CB7993113 of the chemical structure

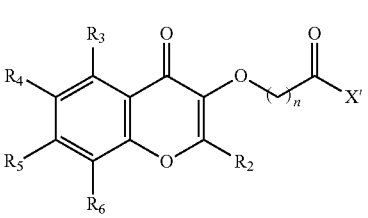

or a stereoisomer or pharmaceutically acceptable salt thereof;

and a pharmaceutically acceptable excipient, carrier or stabilizer, wherein the pharmaceutical composition is formulated as a capsule, pill, caplet or tablet.

3. A pharmaceutical composition comprising an aryl hydrocarbon receptor (AhR) modulator according to Formula (Ia), which has the chemical structure FORMULA (Ia)

wherein:

X' is optionally substituted amino, n is 0-6, $R_2$ is optionally substituted heteroaryl, and
$R_3$, $R_4$, $R_5$ and $R_6$ are independently H,
or a stereoisomer or pharmaceutically acceptable salt thereof;
and a pharmaceutically acceptable excipient, carrier or stabilizer,
wherein the pharmaceutical composition is formulated as a capsule, pill, caplet or tablet.

4. The pharmaceutical composition of claim 1 or claim 2 or claim 3, wherein the pharmaceutical composition is free of lactose.

* * * * *